US010420761B2

United States Patent
Zajac-Kaye et al.

(10) Patent No.: US 10,420,761 B2
(45) Date of Patent: Sep. 24, 2019

(54) ALLOSTERIC INHIBITORS OF THYMIDYLATE SYNTHASE

(71) Applicant: UNIVERSITY OF FLORIDA RESEARCH FOUNDATION, INCORPORATED, Gainesville, FL (US)

(72) Inventors: Maria Zajac-Kaye, Gainesville, FL (US); Lidia Kulemina, Destin, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/773,906

(22) PCT Filed: Mar. 17, 2014

(86) PCT No.: PCT/US2014/030143
§ 371 (c)(1),
(2) Date: Sep. 9, 2015

(87) PCT Pub. No.: WO2014/145386
PCT Pub. Date: Sep. 18, 2014

(65) Prior Publication Data
US 2016/0067240 A1 Mar. 10, 2016

Related U.S. Application Data

(60) Provisional application No. 61/786,910, filed on Mar. 15, 2013.

(51) Int. Cl.
*A61K 31/505* (2006.01)
*A61K 31/472* (2006.01)
(Continued)

(52) U.S. Cl.
CPC .......... *A61K 31/472* (2013.01); *A61K 31/137* (2013.01); *A61K 31/352* (2013.01);
(Continued)

(58) Field of Classification Search
CPC .. A61K 31/519; A61K 31/505; A61K 31/575; A61K 31/708; A61K 31/4468; A61K 31/4745; A61K 31/515
(Continued)

(56) References Cited

U.S. PATENT DOCUMENTS 4,992,444 A * 2/1991 Stevens ................ C07D 239/48
514/275
5,635,515 A * 6/1997 Chauffert ............... A61K 31/49
514/305
(Continued)

FOREIGN PATENT DOCUMENTS

CN 102125579 * 7/2011
JP 57-081460 5/1982
(Continued)

OTHER PUBLICATIONS

Griffin et al, Structural Studies on Bioactive Compounds. 8. Synthesisi, Crystal Structure, and Biological Properties of a New series of 2,4-Diamino-5-aryl-6-ethylpyrimidine Dihydrofolate Reductase Inhibitors with in Vivo Activity tagainst a Methotrexate-Resistant Tumor Cell Line, J. Med. Chem., 1989, 32, p. 2468-2474.*
(Continued)

*Primary Examiner* — Taylor V Oh
(74) *Attorney, Agent, or Firm* — Wolf, Greenfield & Sacks, P.C.

(57) ABSTRACT

The current invention is directed to a class of compounds that inhibit the function of Thymidylate synthase. Thymidylate synthase inhibition was noted to result in inhibition of tumor cell grow and killing of tumor cells. Thymidylate synthase inhibition is, thus, useful for treatment of various types of cancers, including but not limited to, acute lymphoblatic leukemia (ALL), acute myelogenous leukemia (AML), acute promyelocytic leukemia, chronic lymphocytic leukemia (CLL), chronic myelogenous leukemia (CML),
(Continued)

acute monocytic leukemia (AMOL), hairy cell leukemia, large cell immunoblastic lymphoma, plasmacytoma, multiple myeloma, Hodgkin's lymphoma, non-Hodgkin's lymphoma, leukemia, brain cancer, lung cancer, central nervous system (CNS) cancer, melanoma, renal cancer, prostate cancer, colon cancer, ovarian cancer and breast cancer. The compounds disclosed herein can be used alone or in combination with other cancer treatment regimens (e.g., radiation therapy and/or other chemotherapeutic agents that are administered to a subject having a tumor, cancer or neoplasia).

17 Claims, 15 Drawing Sheets

Specification includes a Sequence Listing.

(51) Int. Cl.
| | | |
|---|---|---|
| A61K 31/137 | (2006.01) | |
| A61K 31/352 | (2006.01) | |
| A61K 31/404 | (2006.01) | |
| A61K 31/4196 | (2006.01) | |
| A61K 31/429 | (2006.01) | |
| A61K 31/44 | (2006.01) | |
| A61K 31/4468 | (2006.01) | |
| A61K 31/451 | (2006.01) | |
| A61K 31/4709 | (2006.01) | |
| A61K 31/4745 | (2006.01) | |
| A61K 31/496 | (2006.01) | |
| A61K 31/515 | (2006.01) | |
| A61K 31/519 | (2006.01) | |
| A61K 31/575 | (2006.01) | |
| A61K 31/708 | (2006.01) | |
| A61K 31/4439 | (2006.01) | |
| A61K 31/454 | (2006.01) | |
| A61K 31/48 | (2006.01) | |
| A61K 31/522 | (2006.01) | |
| A61K 31/573 | (2006.01) | |
| A61K 31/7072 | (2006.01) | |
| A61K 31/7076 | (2006.01) | |
| A61K 45/06 | (2006.01) | |
| C07D 213/77 | (2006.01) | |
| C07D 217/20 | (2006.01) | |
| C07D 239/48 | (2006.01) | |
| C07D 405/12 | (2006.01) | |

(52) U.S. Cl.
CPC ........ *A61K 31/404* (2013.01); *A61K 31/4196* (2013.01); *A61K 31/429* (2013.01); *A61K 31/44* (2013.01); *A61K 31/4439* (2013.01); *A61K 31/4468* (2013.01); *A61K 31/451* (2013.01); *A61K 31/454* (2013.01); *A61K 31/4709* (2013.01); *A61K 31/4745* (2013.01); *A61K 31/48* (2013.01); *A61K 31/496* (2013.01); *A61K 31/505* (2013.01); *A61K 31/515* (2013.01); *A61K 31/519* (2013.01); *A61K 31/522* (2013.01); *A61K 31/573* (2013.01); *A61K 31/575* (2013.01); *A61K 31/708* (2013.01); *A61K 31/7072* (2013.01); *A61K 31/7076* (2013.01); *A61K 45/06* (2013.01); *C07D 213/77* (2013.01); *C07D 217/20* (2013.01); *C07D 239/48* (2013.01); *C07D 405/12* (2013.01)

(58) Field of Classification Search
USPC ........................................................ 514/275
See application file for complete search history.

(56) References Cited

U.S. PATENT DOCUMENTS

| | | | |
|---|---|---|---|
| 6,525,091 | B2 | 2/2003 | Robinson et al. |
| 6,984,647 | B2 | 1/2006 | Dax et al. |
| 2003/0216426 | A1 | 11/2003 | Carson et al. |
| 2005/0038031 | A1 | 2/2005 | Dumas et al. |
| 2005/0143588 | A1 | 6/2005 | Heaton et al. |
| 2005/0154010 | A1 | 7/2005 | Carson et al. |
| 2006/0166925 | A1 | 6/2006 | Dolezal et al. |
| 2007/0099976 | A1 | 5/2007 | Halperin et al. |
| 2007/0161546 | A1* | 7/2007 | King ............... A61K 39/39 424/85.4 |
| 2008/0045589 | A1 | 2/2008 | Kelley |
| 2009/0203636 | A1 | 8/2009 | Bondarev |
| 2010/0009934 | A1 | 1/2010 | Rickles et al. |
| 2010/0260772 | A1 | 10/2010 | Karsenty |
| 2011/0176996 | A1* | 7/2011 | O'Neill ............. C07K 16/40 424/1.49 |
| 2011/0224141 | A1 | 9/2011 | Thompson et al. |
| 2012/0082659 | A1 | 4/2012 | Land et al. |
| 2012/0115915 | A1 | 5/2012 | Aktas et al. |
| 2012/0260772 | A1 | 10/2012 | Valerio |
| 2013/0183289 | A1 | 7/2013 | Gorelik et al. |

FOREIGN PATENT DOCUMENTS

| | | | |
|---|---|---|---|
| WO | WO98/30550 | * | 7/1998 |
| WO | WO-98/30550 | | 7/1998 |
| WO | WO 2003/096992 A2 | | 11/2003 |
| WO | WO 2006/049941 A2 | | 5/2006 |
| WO | WO 2006/125540 A1 | | 11/2006 |
| WO | WO 2010/138820 A2 | | 12/2010 |
| WO | WO-2011/151423 | | 12/2011 |

OTHER PUBLICATIONS

Grimaudo et al, Selective Induction of Apoptosis in Multidrug Resistant HL60R Cells by the Thiazolobenzoimidazole Derivative 1-(2,6-difluorophenyl)-1H,3H-thaizolo[3,4-a]benzimidazole(TBZ),European Journal of Cancer, 1998, vol. 34, No. 11, p. 1756-1763).*
Sharma et al , Screening of Potential Chemopreventive Agents using Biochemical Markers of Carcinogenesis, Cancer Research, Nov. 1994 , 54, p. 5848-5855.*
Crawford, K.W., et al., "Sigma-2 Receptor Agonists Activate a Novel Apoptotic Pathway and Potentiate Antineoplastic Drugs in Breast Tumor Cell Lines," *Cancer Research*, 2002, vol. 62, pp. 313-322.
Grimaudo, S., et al., "Selective Induction of Apoptosis in Multidrug Resistant HL60R Cells by the Thiazolobenzoimidazole Derivative 1-(2,6-difluorophenyl)-1H,3H-thiazolo [3,4-a] benzimidazole (TBZ)," *European Journal of Cancer*, 1998, vol. 34, No. 11, pp. 1756-1763.
Houssay, A., et al., "The Influence Exerted by Desoxycorticosterone Acetate upon the Production of Adrenal Tumors in Gonadectomized Mice," *Cancer Research*, 1951, vol. 11, No. 5, pp. 297-300.
Iwama, H., et al., "Epidural Administration of Droperidol Suppresses Cisplatin-induced Emesis: Preliminary Findings," *Surgery Today*, 1998, vol. 28, pp. 231-234.
Li, G., et al., "Simultaneous determination of vanadium, niobium and tantalum by high-performance liquid chromatography equipped with on-line enrichment using 2-[2-(5-bromoquinolinylazo)]-5-diethylaminophenol as pre-column derivatization agent," *Microchimica Acta*, 2007, vol. 158, pp. 95-102.
Pereira, S.F.P., et al., "Spectrophotometric determination of arsenic in soil samples using 2-(5-bromo-2-pyridylazo)-5-di-ethylaminophenol (Br-PADAP)," *Ecletica Quimica*, 2008, vol. 33, No. 3, pp. 23-28.
Pubchem, CID 42501056, May 30, 2009.
Sharma, S., et al., "Screening of Potential Chemopreventive Agents Using Biochemical Markers of Carcinogenesis," *Cancer Research*, 1994, vol. 54, No. 22, pp. 5848-5855.
Yan, K.H., et al., "Mefloquine exerts anticancer activity in prostate cancer cells via ROS-mediated modulation of Akt, ERK, JNK and AMPK signaling," *Oncology Letters*, 2013, vol. 5, pp. 1541-1545.

(56) References Cited

OTHER PUBLICATIONS

Danenberg, P.V., et al., "Thymidylate Synthetase—A Target Enzyme in Cancer Chemotherapy," Biochimica et Biophysica Acta, 1977, vol. 473, pp. 73-92.
Ramaswamy, S., et al., "Multiclass cancer diagnosis using tumor gene expression signatures," *Proceedings of the National Academy of Sciences of the United States of America*, Dec. 18, 2001, vol. 98, No. 26, pp. 15149-15154.
Grunda, J.M., et al., "Increased expression of thymidylate synthetase (TS), ubiquitin specific protease 10 (USP10) and survivin is associated with poor survival in glioblastoma multiforme (GBM)," *Journal of Neuro-Oncology*, 2006, vol. 80, pp. 261-274.
Aarhus, M., et al., "Microarray analysis reveals down-regulation of the tumour suppressor gene WWOX and up-regulation of the oncogene TYMS in intracranial sporadic meningiomas," *Journal of Neuro-Oncology*, 2008, vol. 88, No. 3, pp. 251-259.
Ceppi, P., et al., "Squamous Cell Carcinoma of the Lung Compared With Other Histotypes Shows Higher Messenger RNA and Protein Levels for Thymidylate Synthase," *Cancer*, 2006, 107, No. 7, pp. 1589-1596.
Ceppi, P., et al., "Thymidylate Synthase Expression in Gastroenteropancreatic and Pulmonary Neuroendocrine Tumors," *Clinical Cancer Research*, Feb. 15, 2008, vol. 14, No. 4, pp. 1059-1064.
Skibola, C.F., et al., "Polymorphisms and haplotypes in folate-metabolizing genes and risk of non-Hodgkin lymphoma," *Blood*, Oct. 1, 2004, vol. 104, pp. 2155-2162.
Rahman, L., et al., "Thymidylate synthase as an oncogene: A novel role for an essential DNA synthesis enzyme," *Cancer Cell*, Apr. 2004, vol. 5, No. 4, pp. 341-351.
Voeller, D., et al., "Elevated Levels of Thymidylate Synthase Linked to Neoplastic Transformation of Mammalian Cells," *Cell Cycle*, Aug. 2004, vol. 3, No. 8, pp. 1005-1007.
Edler, D., et al., "Thymidylate Synthase Expression: An Independent Prognostic Factor for Local Recurrence, Distant Metastasis, Disease-free and Overall Survival in Rectal Cancer," *Clinical Cancer Research*, Apr. 2000, vol. 6, No. 4, pp. 1378-1384.
Longley, D.B., et al., "5-fluorouracil: mechanisms of action and clinical strategies," *Nature Reviews Cancer*, May 2003, vol. 3, No. 5, pp. 330-338.
Spielmann, M., et al., "Activity of Pemetrexed (ALIMTA®, Multitargeted Antifolate, LY231514) in Metastatic Breast Cancer Patients Previously Treated with an Anthracycline and a Taxane: An Interim Analysis," *Clinical Breast Cancer*, Apr. 2001, vol. 2, No. 1 pp. 47-51.
Labianca, R., et al., "The role of adjuvant chemotherapy in colon cancer," *Surgical Oncology*, 2007, vol. 16, Suppl. 1, pp. S93-S96.
Ma, C.X., et al., "A phase II trial of a combination of pemetrexed and gemcitabine in patients with metastatic breast cancer: an NCCTG study," *Annals of Oncology*, 2006, vol. 17, No. 2, pp. 226-231.
Barlesi, F., et al., "Pemetrexed and cisplatin as first-line chemotherapy for advanced non-small-cell lung cancer (NSCLC) with asymptomatic inoperable brain metastases: a multicenter phase II trial (GFPC 07-01)," *Annals of Oncology*, 2011, vol. 22, pp. 2466-2470.
Copur, S., et al., "Thymidylate Synthase Gene Amplification in Human Colon Cancer Cell Lines Resistant to 5-Fluorouracil," *Biochemical Pharmacology*, 1995, vol. 49, No. 10, pp. 1419-1426.
Sigmond, J., et al., "Induction of resistance to the multitargeted antifolate Pemetrexed (ALIMTA) in WiDr human colon cancer cells is associated with thymidylate synthase overexpression," *Biochemical Pharmacology*, 2003, vol. 66, No. 3, pp. 431-438.
Chu, E., et al., "Induction of Thymidylate Synthase Associated with Multidrug Resistance in Human Breast and Colon Cancer Cell Lines," *Molecular Pharmacology*, 1991, vol. 39, No. 2, pp. 136-143.
Van Triest, B., et al., "Downstream molecular determinants of response to 5-fluorouracil and antifolate thymidylate synthase inhibitors," *Annals of Oncology*, 2000, vol. 11, No. 4, pp. 385-391.

Carreras, C.W., et al., "The catalytic mechanism and structure of thymidylate synthase," *Annual Review of Biochemistry*, 1995, vol. 64, pp. 721-762.
Phan, J., et al., "Human Thymidylate Synthase Is in the Closed Conformation When Complexed with dUMP and Raltitrexed, an Antifolate Drug," *Biochemistry*, 2001, vol. 40, pp. 1897-1902.
Irwin, J.J., et al., "ZINC: A Free Tool to Discover Chemistry for Biology," *Journal of Chemical Information and Modeling*, 2012, vol. 52, No. 7, pp. 1757-1768.
Wahba, A.J., et al., "The Enzymatic Synthesis of Thymidylate. I. Early steps in the purification of thymidylate synthetase of *Escherichia coli*," *Journal of Biological Chemistry*, Dec. 1962, vol. 237, No. 12, pp. 3794-3801.
Klebe, G., "Virtual ligand screening: strategies, perspectives and limitations," *Drug Discovery Today*, Jul. 2006, vol. 11, Nos. 13-14, pp. 580-594.
Mukherjee, S., et al., "Docking Validation Resources: Protein Family and Ligand Flexibility Experiments," *Journal of Chemical Information and Modeling*, 2010, vol. 50, No. 11, pp. 1986-2000.
Brozell, S.R., et al., "Evaluation of DOCK 6 as a pose generation and database enrichment tool," *Journal of Computer-Aided Molecular Design*, 2012, vol. 26, pp. 749-773.
Cardinale, D., et al., "Protein-protein interface-binding peptides inhibit the cancer therapy target human thymidylate synthase," *Proceedings of the National Academy of Sciences of the United States of America*, Aug. 23, 2011, vol. 108, No. 34, pp. E542-E549.
Wahba, A.J., et al., "Direct Spectrophotometric Evidence for the Oxidation of Tetrahydrofolate during the Enzymatic Synthesis of Thymidylate," *Journal of Biological Chemistry*, vol. Mar. 1961, vol. 236, pp. PC11-PC12.
Galvani, E. et al. "Thymidylate synthase inhibitors for non-small cell lung cancer" *Expert Opinion on Investigational Drugs*, 2011, vol. 20, No. 10, pp. 1343-1356.
International Preliminary Report on Patentability, dated Sep. 24, 2015, in connection with PCT/US2014/030143.
International Search Report and Written Opinion, dated Oct. 27, 2014, in connection with PCT/US2014/030143.
International Search Report and Written Opinion, dated Oct. 19, 2016, in connection with PCT/US2016/037731.
Chang et al., PI3K/Akt/mTOR pathway inhibitors enhance radiosensitivity in radioresistant prostate cancer cells through inducing apoptosis, reducing autophagy, suppressing NHEJ and HR repair pathways. Cell Death Dis. Oct. 2, 2014;5:e1437. doi:10.1038/cddis.2014.415.
Morgan et al., Targeted therapy for advanced prostate cancer: inhibition of the PI3K/Akt/mTOR pathway. Curr Cancer Drug Targets. Mar. 2009;9(2):237-49.
U.S. Appl. No. 15/737,545, filed Dec. 18, 2017, Zajac-Kaye et al.
[No Author Listed], CID 5911417. Compound Summary. Sep. 10, 2005. https://pubchem.ncbi.nlm.nih.gov/compound/5911417#section=Top. [last accessed Jul. 17, 2017]. 15 pages.
[No Author Listed], CID 280274. Compound Summary. Mar. 26, 2006. https://pubchem.ncbi.nlm.nih.gov/compound/280274#section=Top. [last accessed Jul. 17, 2017]. 14 pages.
Barrows et al., A Screen of FDA-Approved Drugs for Inhibitors of Zika Virus Infection. Cell Host Microbe. Aug. 10, 2016;20(2):259-70. doi: 10.1016/j.chom.2016.07.004. Epub Jul. 28, 2016.
Bermudez et al., Mefloquine and Its Enantiomers Are Active against *Mycobacterium tuberculosis* In Vitro and in Macrophages. Tuberc Res Treat. 2014;2014:530815. doi: 10.1155/2014/530815. Epub Dec. 11, 2014.
Brickelmaier et al., Identification and characterization of mefloquine efficacy against JC virus in vitro. Antimicrob Agents Chemother. May 2009;53(5):1840-9. doi: 10.1128/AAC.01614-08. Epub Mar. 2, 2009.
Chavchich et al., Role of pfmdr1 amplification and expression in induction of resistance to artemisinin derivatives in Plasmodium falciparum. Antimicrob Agents Chemother. Jun. 2010;54(6):2455-64. doi: 10.1128/AAC.00947-09. Epub Mar. 29, 2010.

(56) References Cited

OTHER PUBLICATIONS

Cruikshank et al., Potent block of Cx36 and Cx50 gap junction channels by mefloquine. Proc Natl Acad Sci U S A. Aug. 17, 2004;101(33):12364-9. Epub Aug. 5, 2004.

Geng et al., Chloroquine-induced autophagic vacuole accumulation and cell death in glioma cells is p53 independent. Neuro Oncol. May 2010;12(5):473-81. doi: 10.1093/neuonc/nop048. Epub Jan. 27, 2010.

Gonçalves et al., Mefloquine-oxazolidine derivatives, derived from mefloquine and arenecarbaldehydes: In vitro activity including against the multidrug-resistant tuberculosis strain T113. Bioorg Med Chem. Jan. 1, 2012;20(1):243-8. doi: 10.1016/j.bmc.2011.11.006. Epub Nov. 12, 2011.

Kim et al., Co-treatment with the anti-malarial drugs mefloquine and primaquine highly sensitizes drug-resistant cancer cells by increasing P-gp inhibition. Biochem Biophys Res Commun. Nov. 22, 2013;441(3):655-60. doi: 10.1016/j.bbrc.2013.10.095. Epub Oct. 26, 2013.

Krieger et al., Mefloquine as a potential drug against multidrug-resistant tuberculosis. Eur Respir J. Nov. 2015;46(5):1503-5. doi: 10.1183/13993003.00321-2015. Epub Jul. 23, 2015.

Liu et al., Mefloquine effectively targets gastric cancer cells through phosphatase-dependent inhibition of PI3K/Akt/mTOR signaling pathway. Biochem Biophys Res Commun. Feb. 5, 2016;470(2):350-5. doi:10.1016/j.bbrc.2016.01.046. Epub Jan. 11, 2016.

Rodrigues et al., Mefloquine-oxazolidine derivatives: a new class of anticancer agents. Chem Biol Drug Des. Jan. 2014;83(1):126-31. doi:10.1111/cbdd.12210. Epub Oct. 5, 2013.

Sachlos et al., Identification of drugs including a dopamine receptor antagonist that selectively target cancer stem cells. Cell. Jun. 8, 2012;149(6):1284-97. doi: 10.1016/j.cell.2012.03.049. Epub May 24, 2012.

Sharma et al., Inhibition of autophagy and induction of breast cancer cell death by mefloquine, an antimalarial agent. Cancer Lett. Dec. 30, 2012;326(2):143-54. doi:10.1016/j.canlet.2012.07.029. Epub Aug. 1, 2012.

Sukhai et al., Lysosomal disruption preferentially targets acute myeloid leukemia cells and progenitors. J Clin Invest. Jan. 2013;123(1):315-28. doi:10.1172/JCI64180. Epub Dec. 3, 2012.

Yan et al., Mefloquine induces cell death in prostate cancer cells and provides a potential novel treatment strategy in vivo.. Oncol Lett. May 2013;5(5):1567-1571. Epub Mar. 15, 2013.

\* cited by examiner

Small molecule compound library (shown as sticks) docked into the target site

HeLa cancer cell viability after 72 hours with new TS inhibitors

| Cancer type: | Cervical cancer | | | | | |
|---|---|---|---|---|---|---|
| Cell line: | HeLa | | | | | |
| Compound[1] | G 609874 | J 612049 | M131747 | P 157387 | S 382035 | 5-FU |
| Concentration | 100μM | 100μM | 100μM | 100μM | 100μM | 100μM |
| % viability | 23.31 | 35.05 | 41.65 | 27.96 | 23.72 | 36.96 |

[1] Here and throughout the document compound abbreviations are as follows: S (NSC 382035), U (NSC 367081), P (NSC 157387) G (NSC 609874) and M (NSC 131747)

K562 cancer cell viability after 72 hours with new TS inhibitors

| Cancer type: | Myelogenous leukaemia (hematological, CML) | | | | | | |
|---|---|---|---|---|---|---|---|
| Cell line: | K562 cells | | | | | | |
| Compound | G 609874 | J 612049 | M131747 | P 157387 | S 382035 | U 367081 | 5-FU |
| Concentration | 100μM | 100μM | 100μM | 100μM | 100μM | 100μM | 100μM |
| % viability | 25.95 | 34.89 | 39.12 | 21.18 | 29.58 | 59.59 | 32.85 |

Dose-response curves of compounds S, P and U in mouse histiocytic sarcoma cell line derived from genetically engineered mouse with deleted p16 and activated hTS

SEQUENCE LISTING

<160> NUMBER OF SEQ ID NOS: 1

<210> SEQ ID NO 1
<211> LENGTH: 319
<212> TYPE: PRT
<213> ORGANISM: Homo sapiens

<400> SEQUENCE: 1

```
His His His His His His Met Pro Val Ala Gly Ser Glu Leu Pro Arg
 1               5                  10                  15

Arg Pro Leu Pro Pro Ala Ala Gln Glu Arg Asp Ala Glu Pro Arg Pro
             20                  25                  30

Pro His Gly Glu Leu Gln Tyr Leu Gly Gln Ile Gln His Ile Leu Arg
         35                  40                  45

Cys Gly Val Arg Lys Asp Asp Arg Thr Gly Thr Gly Thr Leu Ser Val
 50                  55                  60

Phe Gly Met Gln Ala Arg Tyr Ser Leu Arg Asp Glu Phe Pro Leu Leu
 65                  70                  75                  80

Thr Thr Lys Arg Val Phe Trp Lys Gly Val Leu Glu Glu Leu Leu Trp
             85                  90                  95

Phe Ile Lys Gly Ser Thr Asn Ala Lys Glu Leu Ser Ser Lys Gly Val
            100                 105                 110

Lys Ile Trp Asp Ala Asn Gly Ser Arg Asp Phe Leu Asp Ser Leu Gly
            115                 120                 125

Phe Ser Thr Arg Glu Glu Gly Asp Leu Gly Pro Val Tyr Gly Phe Gln
        130                 135                 140

Trp Arg His Phe Gly Ala Glu Tyr Arg Asp Met Glu Ser Asp Tyr Ser
145                 150                 155                 160

Gly Gln Gly Val Asp Gln Leu Gln Arg Val Ile Asp Thr Ile Lys Thr
                165                 170                 175

Asn Pro Asp Asp Arg Arg Ile Ile Met Cys Ala Trp Asn Pro Arg Asp
            180                 185                 190

Leu Pro Leu Met Ala Leu Pro Pro Cys His Ala Leu Cys Gln Phe Tyr
        195                 200                 205

Val Val Asn Ser Glu Leu Ser Cys Gln Leu Tyr Gln Arg Ser Gly Asp
    210                 215                 220

Met Gly Leu Gly Val Pro Phe Asn Ile Ala Ser Tyr Ala Leu Leu Thr
225                 230                 235                 240

Tyr Met Ile Ala His Ile Thr Gly Leu Lys Pro Gly Asp Phe Ile His
                245                 250                 255

Thr Leu Gly Asp Ala His Ile Tyr Leu Asn His Ile Glu Pro Leu Lys
            260                 265                 270

Ile Gln Leu Gln Arg Glu Pro Arg Pro Phe Pro Lys Leu Arg Ile Leu
        275                 280                 285

Arg Lys Val Glu Lys Ile Asp Asp Phe Lys Ala Glu Asp Phe Gln Ile
    290                 295                 300

Glu Gly Tyr Asn Pro His Pro Thr Ile Lys Met Glu Met Ala Val
305                 310                 315
```

ALLOSTERIC INHIBITORS OF THYMIDYLATE SYNTHASE

CROSS-REFERENCE TO RELATED APPLICATIONS

This application is the U.S. national stage application of International Patent Application No. PCT/US2014/030143, filed Mar. 17, 2014, which claims the benefit of U.S. Provisional Application Ser. No. 61/786,910, filed Mar. 15, 2013, the disclosures of which are hereby incorporated by reference in their entirety, including all figures, tables and amino acid or nucleic acid sequences.

FIELD OF THE INVENTION

The invention relates to new anti-proliferative compounds, salts, derivatives, stereoisomers and racemic and non-racemic mixtures thereof that could be used in treatment of proliferative disorders, such as cancer, including but not limited to pancreatic, colon, lung and hematopoietic cancers. The compounds of the current invention or derivatives thereof can also be used for the treatment of Paget's disease, for example, Paget's disease of the bone, Paget's disease of the breast, or extramammary Paget's disease.

BACKGROUND OF THE INVENTION

Thymidylate synthase (TS) is an essential enzyme for DNA synthesis and repair [1] that is expressed at low levels in normal tissues. TS has been reported to be aberrantly overexpressed in a wide range of human cancers including colon, lung, pancreatic, breast, ovarian, neuroendocrine tumors, glioblastoma, lymphoma and sarcoma, and many other tumor types [2-7]. Activated expression of TS plays a direct role in promoting tumorigenesis and results in more aggressive disease [8, 9]. Multiple clinical studies have also confirmed that TS overexpression significantly correlates with the disease stage [10]. TS is a validated therapeutic target for chemotherapy agents, such as 5-fluorouracil, and pemetrexed [11]. These agents are effective in prolonging the survival of patients with colorectal, breast and lung cancer [12-15]. Despite many successes in targeting TS with chemotherapy agents, the ability of fluoropyrimidine TS inhibitors to achieve durable complete remissions is rare in patients with metastatic disease due to induction of TS overexpression [16] and development of resistance that ultimately limits clinical effectiveness [17-20].

The current invention provides novel compounds and derivatives thereof capable of specifically inhibiting TS in vitro and in human cancer cell lines in vivo. The current invention also provides the search strategy related to the discovery of these novel TS inhibitors. The newly discovered small molecule TS inhibitors of the current invention can have profound implications for the treatment and prevention of a broad range of tumors since TS is a target for aberrant overexpression in many human cancer subtypes, including those that were not sensitive to currently used therapies.

BRIEF SUMMARY OF THE INVENTION

The current invention provides small molecule allosteric inhibitors that were designed to disrupt TS cooperativity, for example, by "overstabilizing" the dimer structure by limiting shearing motions at the interface (FIG. 1) and preserving the enzyme in the semi-open conformation so that TS becomes unable to proceed through catalysis. The current invention provides 21 non-limiting examples of novel specific allosteric inhibitors of TS. Six of these twenty-one representative compounds (Table 2) demonstrate strong anti-proliferative properties in multiple human cancer cell lines (FIGS. 6-14) and (Table 3). The novel small molecule TS inhibitors described in the current invention were designed to provide selective and potent inhibition of the enzyme through an alternative mechanism that does not interfere with TS-mRNA binding (primary source of TS overexpression-associated resistance) and, therefore, should not induce protein overexpression. The examples of the novel TS inhibitors of the current invention are shown in Table 1.

The new TS inhibitors of the current invention can be used for the treatment of proliferative diseases, for example, cancer. These novel TS inhibitors can also be used to treat Paget's disease.

BRIEF DESCRIPTION OF THE DRAWINGS

The following description of the invention is done with reference to the attached figures in which.

In various embodiments, R1, R3, R4 and R5 are independently, a hydrogen atom, methyl, $C_1$-$C_5$ branched or unbranched alkyl, amino, nitro, amidino, sulpho, sulphonamido, carboxy, cyano, phenyl, thienyl, pyrril, pyrazolyl, imidazolyl, isoxazyl, triazolyl, tetrazolyl, thiazolyl, oxazolyl, quinazolyl, pyridyl, pyrimidyl group, $C_1$-$C_5$ alkenyl, $C_1$-$C_5$ alkylamino, $C_2$-$C_{10}$ dialkylamino, hydroxy $C_1$-$C_5$ alkyl, carbonyl, $C_3$-$C_7$ cycloalkyl or trifluoromethyl group; R2 is a hydrogen atom, $C_1$-$C_5$ alkyl, hydroxy, amino, nitro, sulpho, sulphonamido, carboxy, or cyano group, X is a carbon, nitrogen, oxygen or sulphur atom at the indicated position, producing respective alkyl, alkylamino, alkoxy, sulphaalkyl derivatives, Y is a carbon, nitrogen or oxygen atom at the indicated position, producing respective alkyl, alkylamino, alkoxy, sulphaalkyl derivative, Hal represents a halogen group producing respective fluoro, chloro, bromo, and iodo and L1 and L2 represent linkage bridging the two carbons at the specified position surrounded by parentheses and is $C_1$-$C_5$ alkylene, $C_2$-$C_5$ alkenylene, amidino or ureido type of linkage

BRIEF DESCRIPTION OF THE SEQUENCE

SEQ ID NO: 1. Amino-acid sequence of the recombinant human thymidylate synthase (hTS) with N-terminal 6-histidine tag.

DETAILED DISCLOSURE OF THE INVENTION

Figure 1:
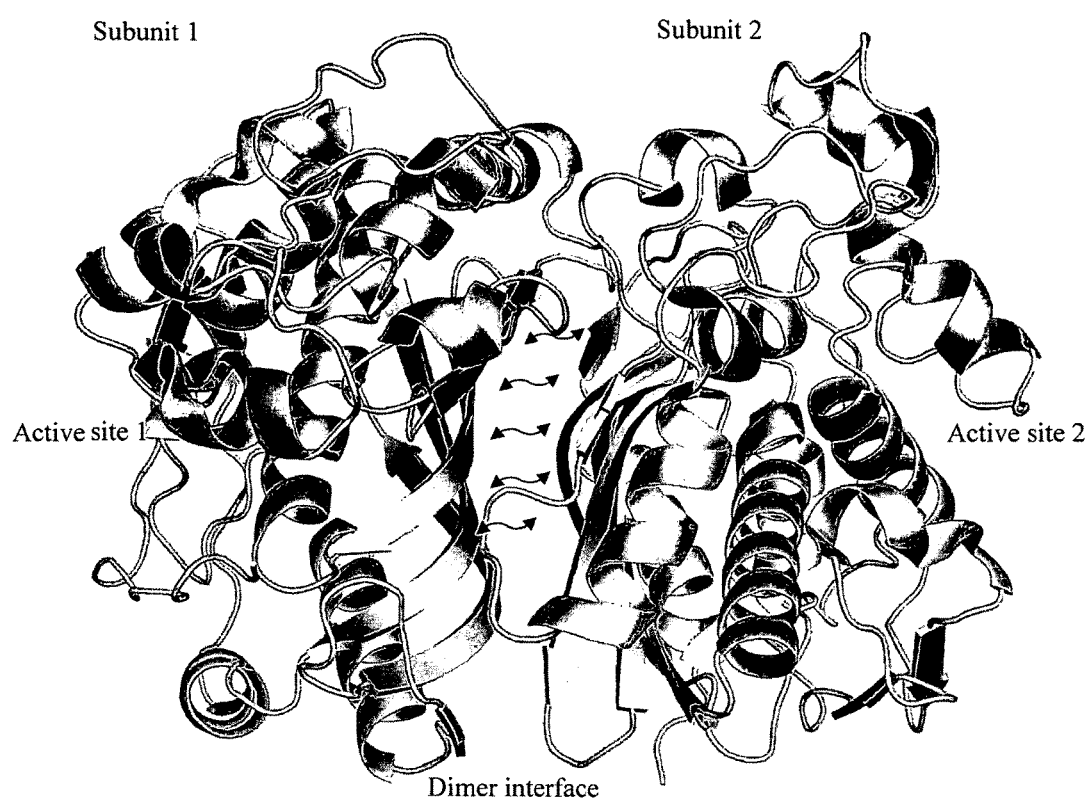
FIG. 1. TS subunit cooperativity is executed through small scale shearing motions at the dimer interface.

Thymidylate synthase (TS) is a methyltransferase that serves as a sole de novo source of deoxythymidylate monophosphate (dTMP) inside the cell and, therefore, is the main contributor to dTTP pools for DNA biosynthesis. Disruption of TS activity in abnormally proliferating cancer cells impairs production of dTMP building blocks for DNA biosynthesis and results in nucleotide misincorporations, formation of DNA strand breaks and "thymineless death" [21]. Thymidylate synthase is a homodimeric enzyme with two symmetrical active sites, each formed by the residues from both monomers [22]. In TS catalytic mechanism, binding of the substrate at one active site, initiates a conformational change at the catalytic loop (residues 181-197) that gets translated across the dimer interface to close the second active site. As a result, TS functions in a "see-saw" fashion: when one active site is occupied, the other one is closed. This highly cooperative behavior is executed through small scale shearing motions at the dimer interface that are integral to TS enzymatic function (FIG. 1).

Figure 2:
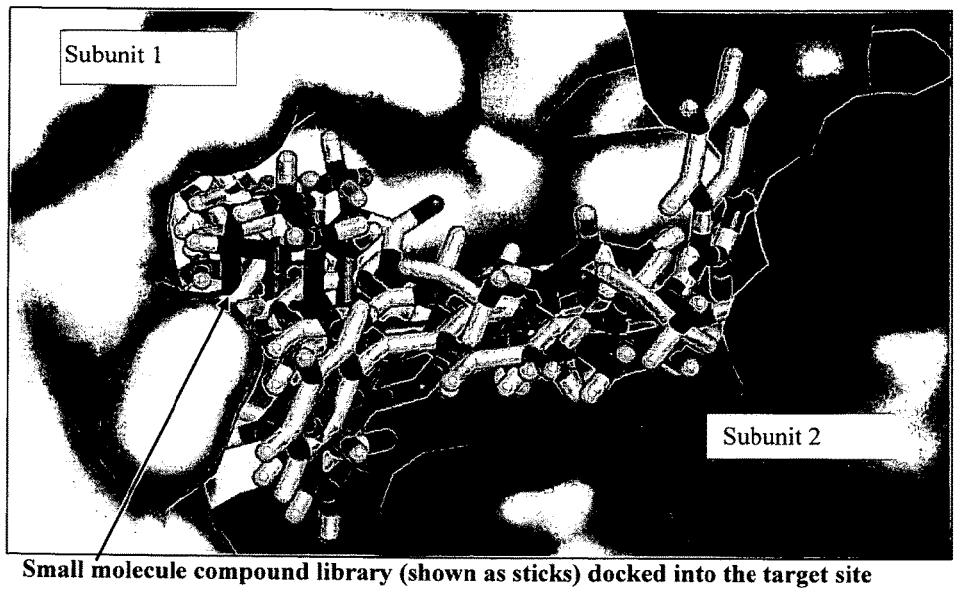
FIG. 2. TS target site selected for in silico docking of National Cancer Institute small molecule library.

This invention describes the compounds designed to "overstabilize" TS dimer conformation and inhibit TS enzymatic activity by targeting a critical structural pocket at the dimer interface (FIG. 2). These compounds were identified by molecular docking of small molecule compound library followed by in vitro and in vivo testing of highest scoring compounds with favorable physicochemical properties. This invention provides the compounds that (1) specifically inhibit human thymidylate synthase; (2) inhibit cell proliferation of multiple human cancer cell lines better than commonly used chemotherapeutic agents such as 5-fluorouracil and pemetrexed and (3) do not show toxicity in SCID mice when administered at 50 mg/kg for 3 weeks. This report also describes the methodology used in compound selection and testing.

Identification of the Template for Molecular Docking and Allosteric Target Site.

To identify a reliable structural model for molecular docking, we analyzed 14 high-resolution three-dimensional structures for TS dimers and selected a structure in the semi-open conformation with highest resolution (1.90 A) and excellent geometry [23]. We performed extensive structural, functional conservation and solvent accessibility analysis of the dimer surface to identify the best "druggable" regions with high surface concavity that would be suitable for small molecule binding. CCP4 suite AreaiMol software was used to identify accessible surface area and "druggable" regions across entire TS molecular surface. Evolutionary conservation analysis revealed several highly conserved residue clusters that matched functionally important regions. A single site at the dimer interface that ranked highly on all of the above criteria was selected as a template for molecular docking.

Computational Screening.

Figure 3:
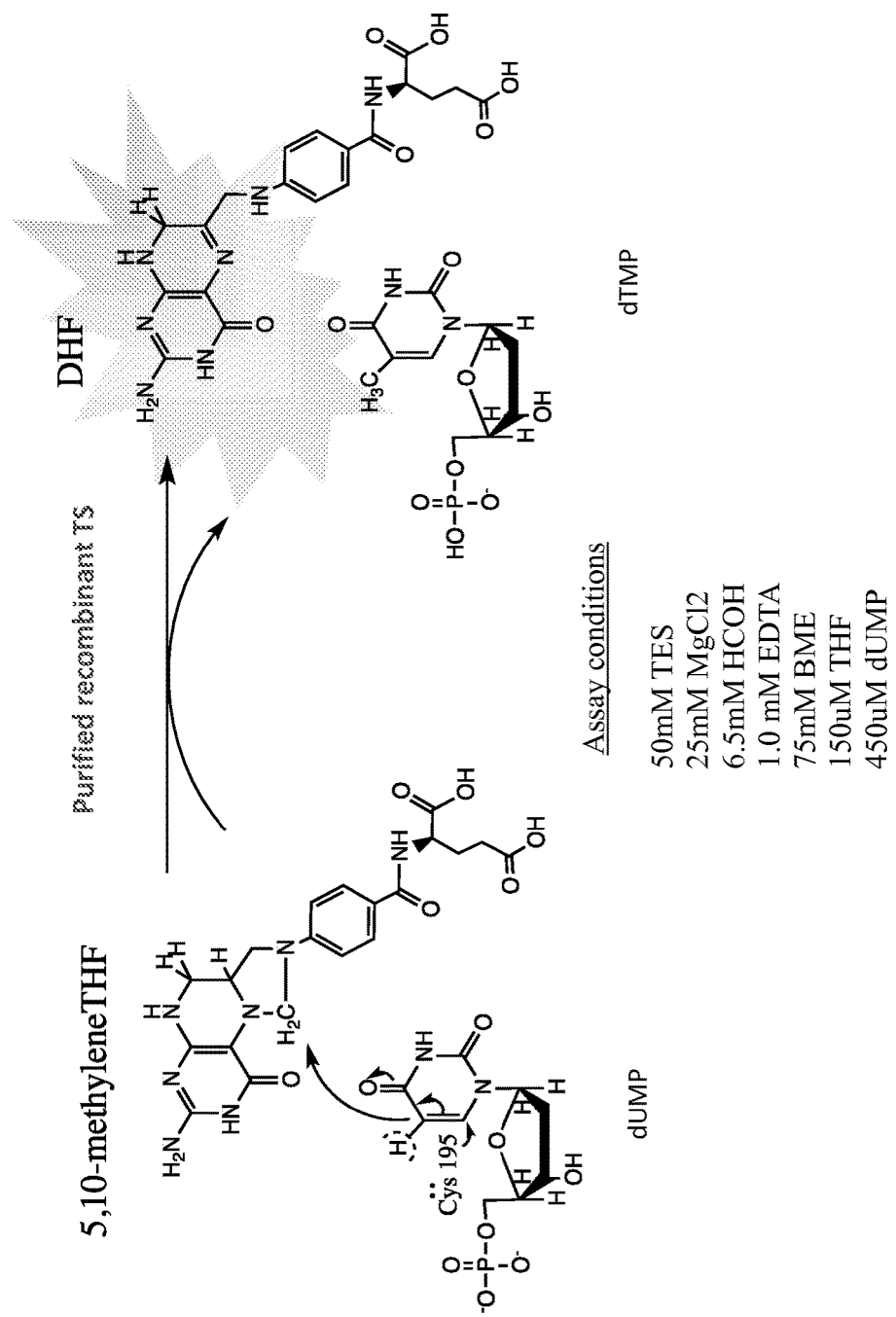
FIG. 3. TS kinetics assay scheme and conditions used for compound in vitro screening.

National Cancer institute (NCI) library of 139,735 compounds was obtained from ZINC database [24] and pruned for redundant structures and molecules with molecular weight under 200 Da. We used molecular docking (DOCK6.5 with AMBER scoring) to computationally screen this curated library within the constraints of the selected site to identify the compounds most likely to bind to the target (FIG. 2). Compounds were each positioned into the target site at the dimer interface surface region in 1000 orientations and ranked based on their predicted energy scores. The top 1000 hits were visualized in PyMOL (web site pymol.org) and manually checked for consistency of molecular docking predictions and overall fit. Since tight binding might not be achievable with conventional drug-like small molecules defined by Lipinski rules [25], we employed additional selection criteria such as lower polarity and large size of the molecule in order to better address unique features of protein dimer interface. 827 compounds that passed these criteria were re-ranked based on multiple physicochemical characteristics, including polarity, solubility, pKa, toxicity and other parameters. 27 compounds were requested from National Cancer Institute and tested in vitro using highly reliable and sensitive kinetics assay [25] (FIG. 3).

Enzymological Evaluation of Top-Scoring Compounds.

Figure 4:
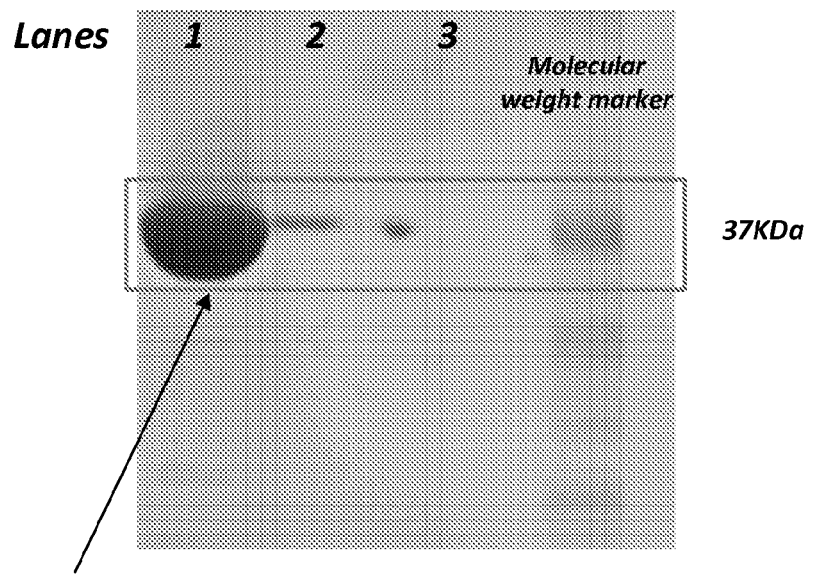
FIG. 4. SDS-PAGE protein gel for recombinant human TS purified in our laboratory.
Figure 5:
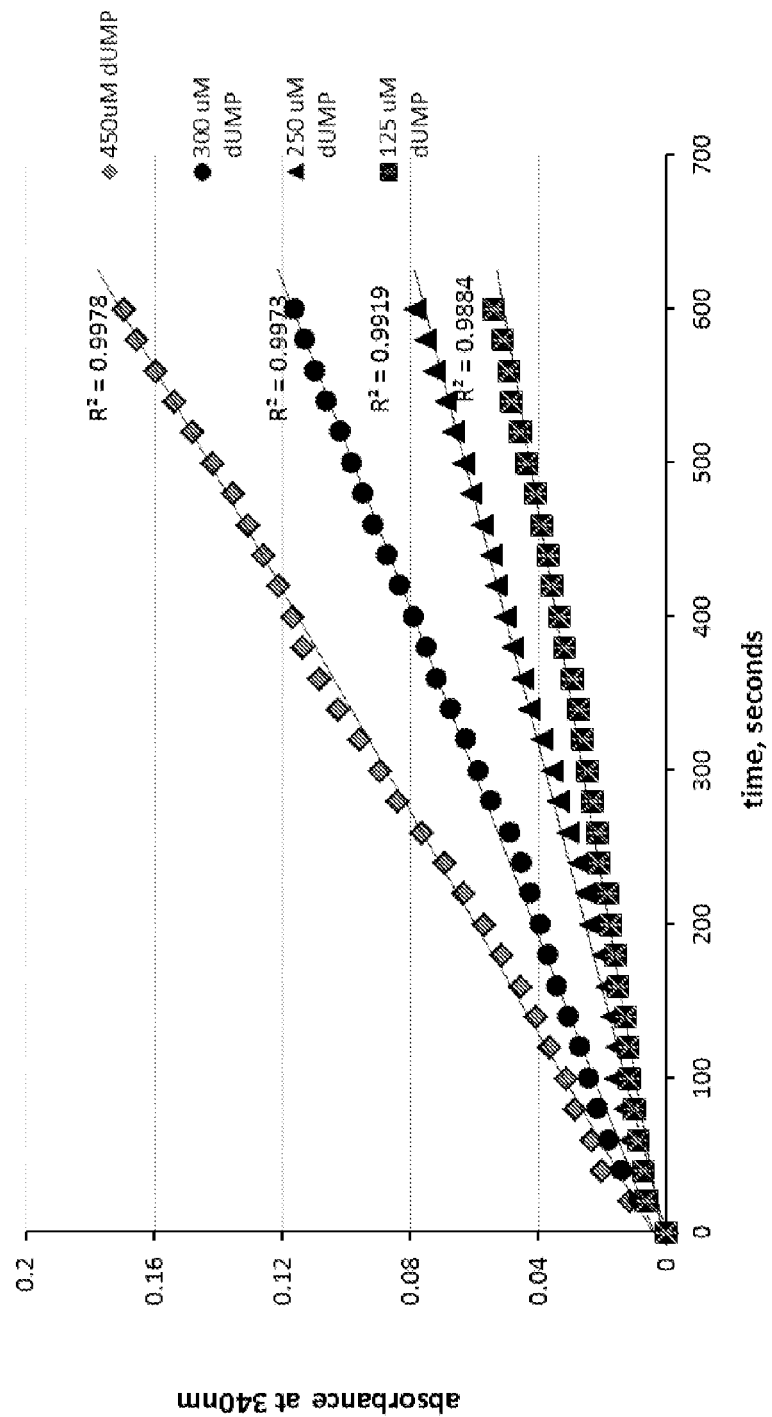
FIG. 5. TS initial velocity at different dUMP substrate concentrations.

Effects of selected small molecule compounds on TS enzymatic activity were evaluated in vitro by using purified active recombinant human TS (SEQ ID NO: 1) (FIG. 4). TS activity was assayed using the method developed by Wahba and Friedkin with small modifications [26] (FIG. 3) and by closely following Assay Guidance Manual [27] published by Eli Lilly & Company and the National Center for Advancing Translational Sciences. We confirmed TS enzyme stability at assay conditions prior to compound testing (50 mM TES, 25 mM $MgCl_2$, 6.5 mM HCOH, 1.0 mM EDTA, 75 mM BME, 150 µM THF and 450 µM dUMP, pH7.4, 37° C.). TS showed excellent linearity over the course of experiment (FIG. 5) and those conditions were used in all inhibitor compound screenings. 21 out of 27 selected compounds were confirmed to significantly inhibit TS. All 21 compounds were equivalent or better inhibitors than 5-FU at the same concentration. 17 out of 21 compounds inhibited TS at a concentration of 500 nM or less.

Cancer Cell Viability Assay

Figure 6:
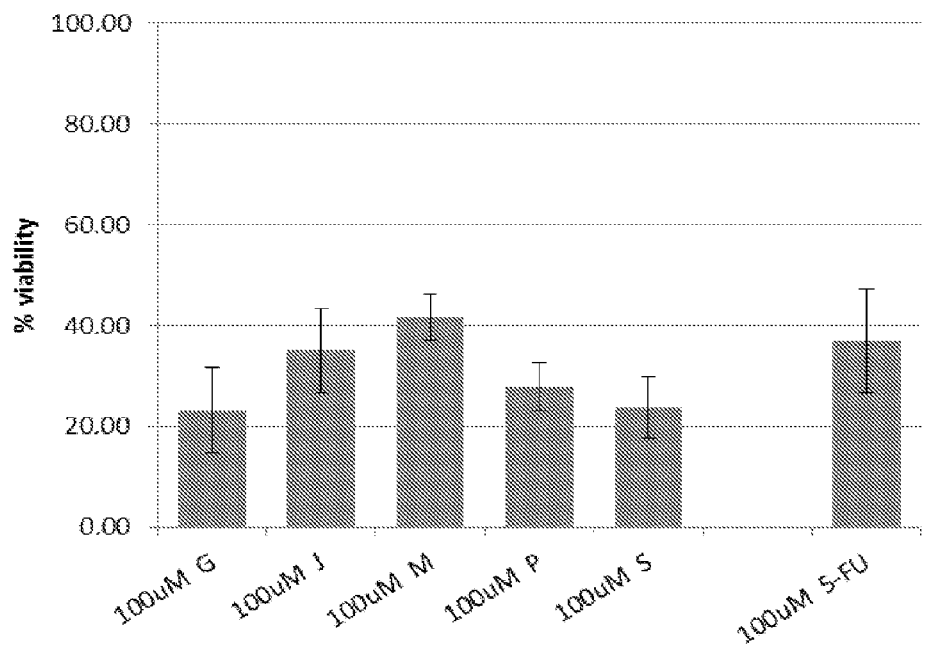
FIG. 6. Growth inhibition of cervical cancer (HeLa) cell line by new allosteric TS inhibitors G (NSC609874), J (NSC612049), M (NSC131747), P (NSC157387), S (NSC382035).
Figure 7:
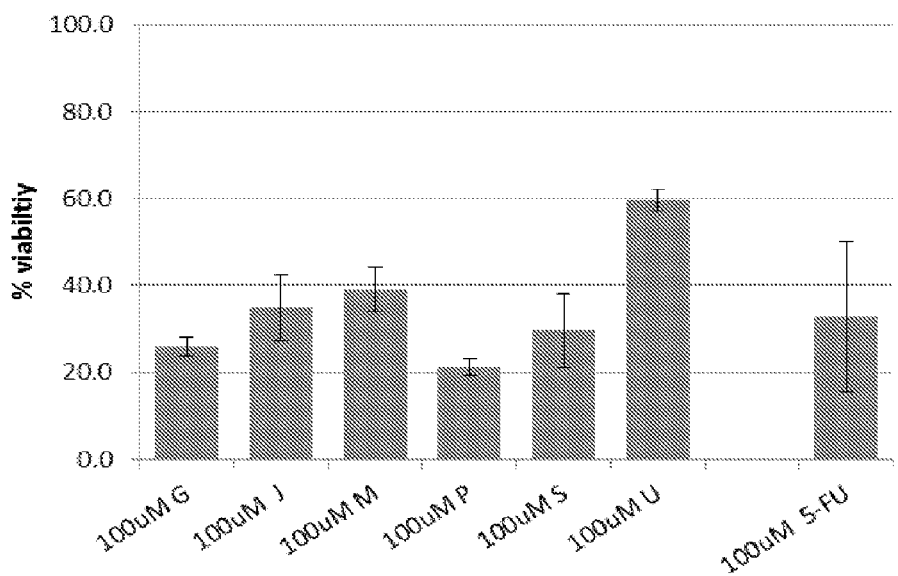
FIG. 7. Anti-proliferative effects of compounds G, J, M, P, S, U in chronic myelogenous leukemia (K562) cell line.

Antiproliferative effects of 27 novel TS inhibitors were tested by MTS assay (Promega) in human cancer cell lines representing several major tumor types known to overexpress TS including lung, cervical, pancreatic and hematopoietic tumors. Six compounds (S, U, P, M, G and J) reduced cell viability by more than 40% in both human cervical cancer HeLa (FIG. 6) and myelogenous leukemia K562 cell lines (FIG. 7).

Figure 8:
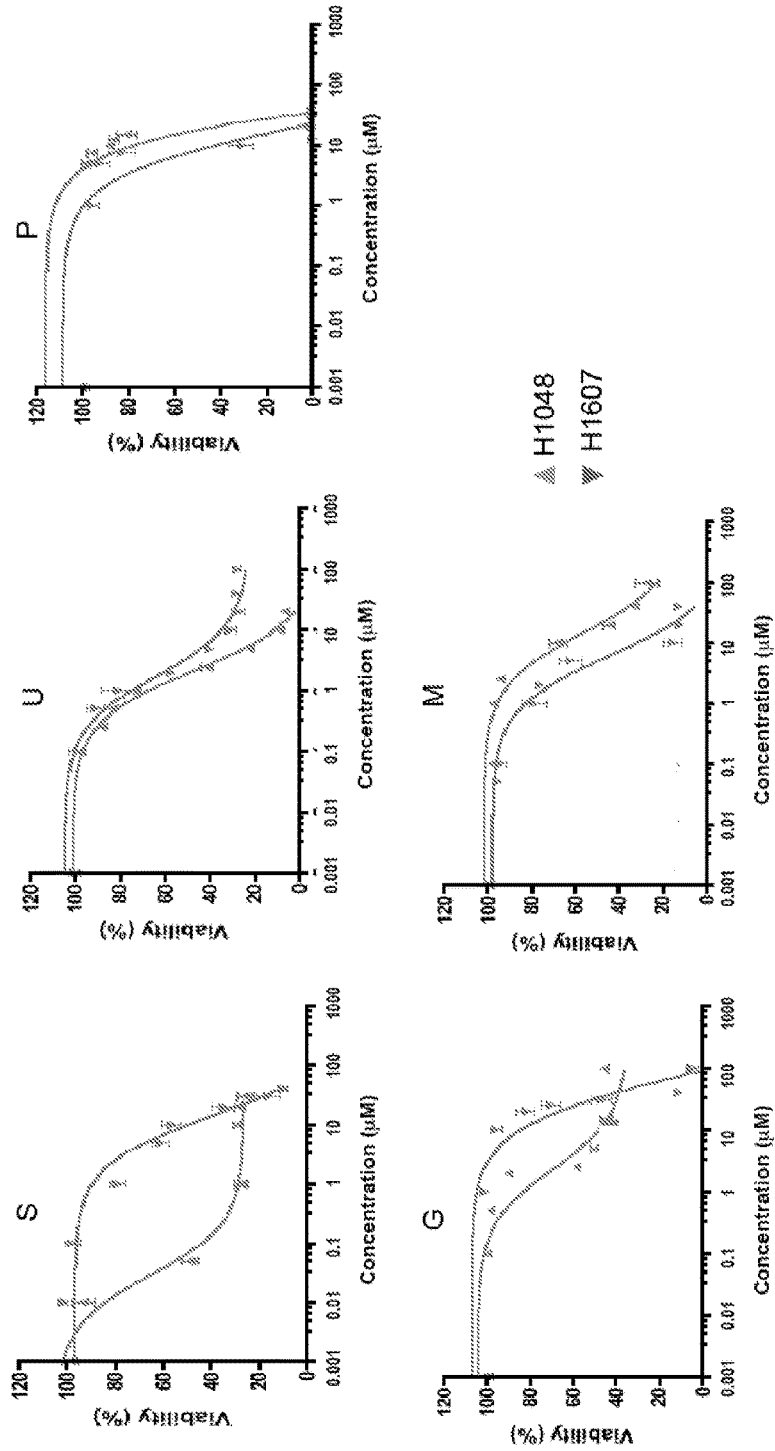
FIG. 8. Dose-dependent growth inhibition of human small cell lung cancer cell lines H1607 and H1048 by compounds S, U, P, G and M.
Figure 9:
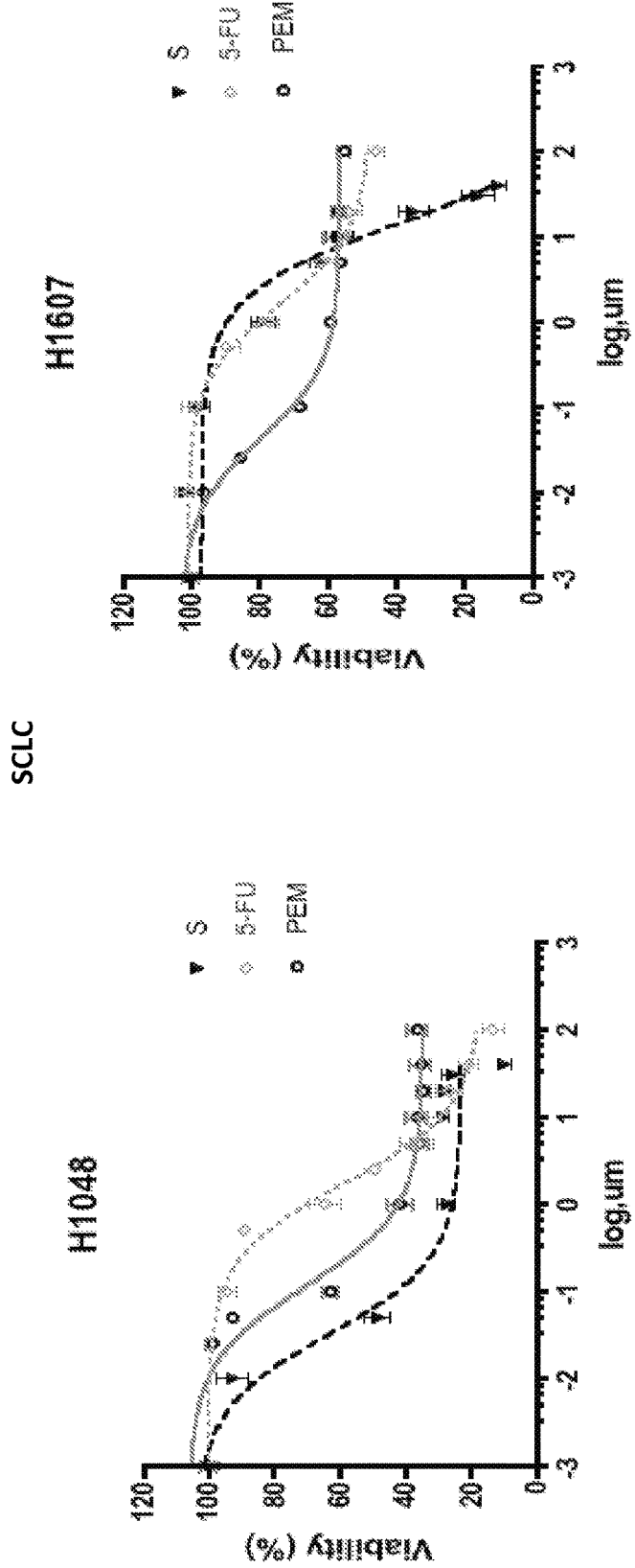
FIG. 9. Effect of compound S on growth inhibition of small cell lung cancer cell lines H1607 and H1048 compared to pemetrexed and 5-FU FIG. 10. Dose-dependent growth inhibition of pancreatic neuroendocrine cell lines Bon1 and CM by compounds S, U, P, G and M.
Figure 10:
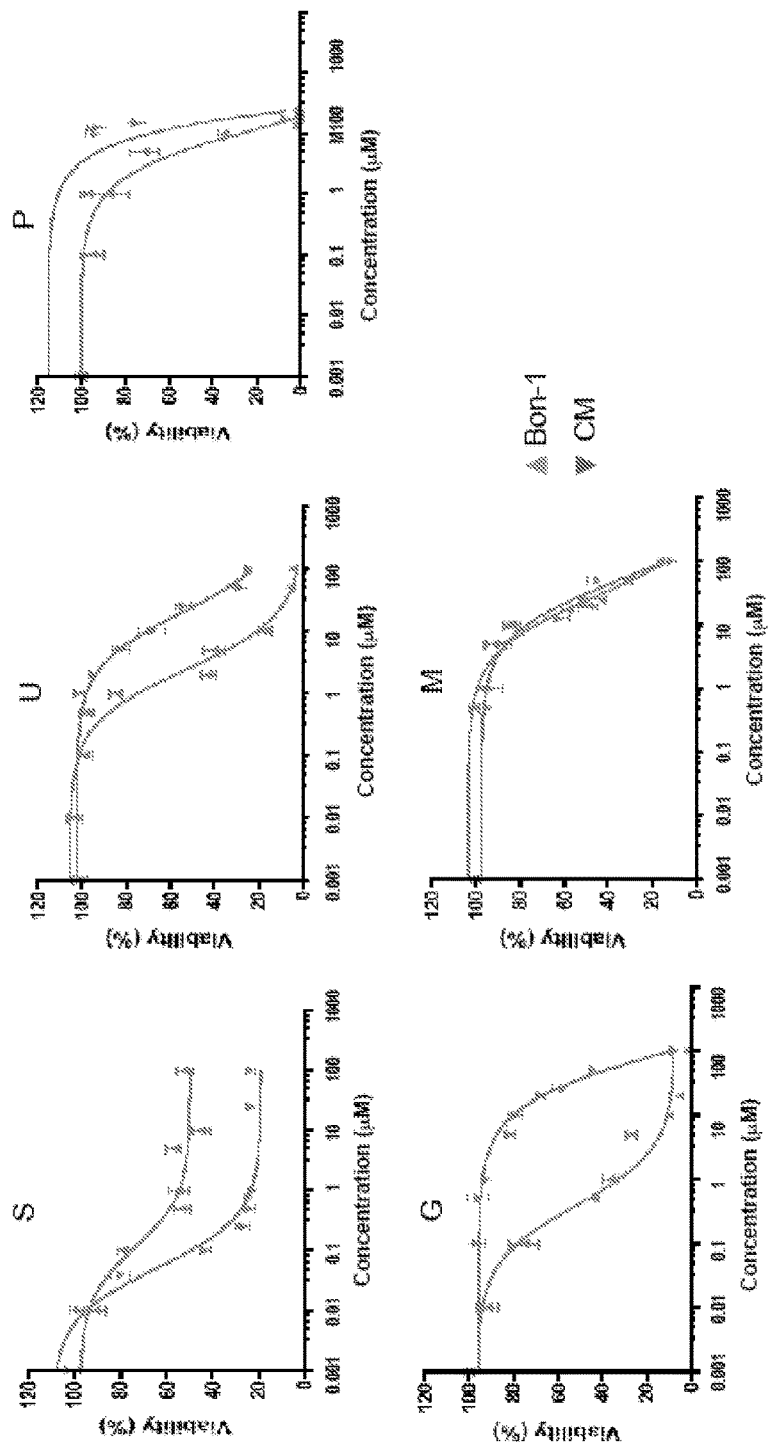
Figure 11:
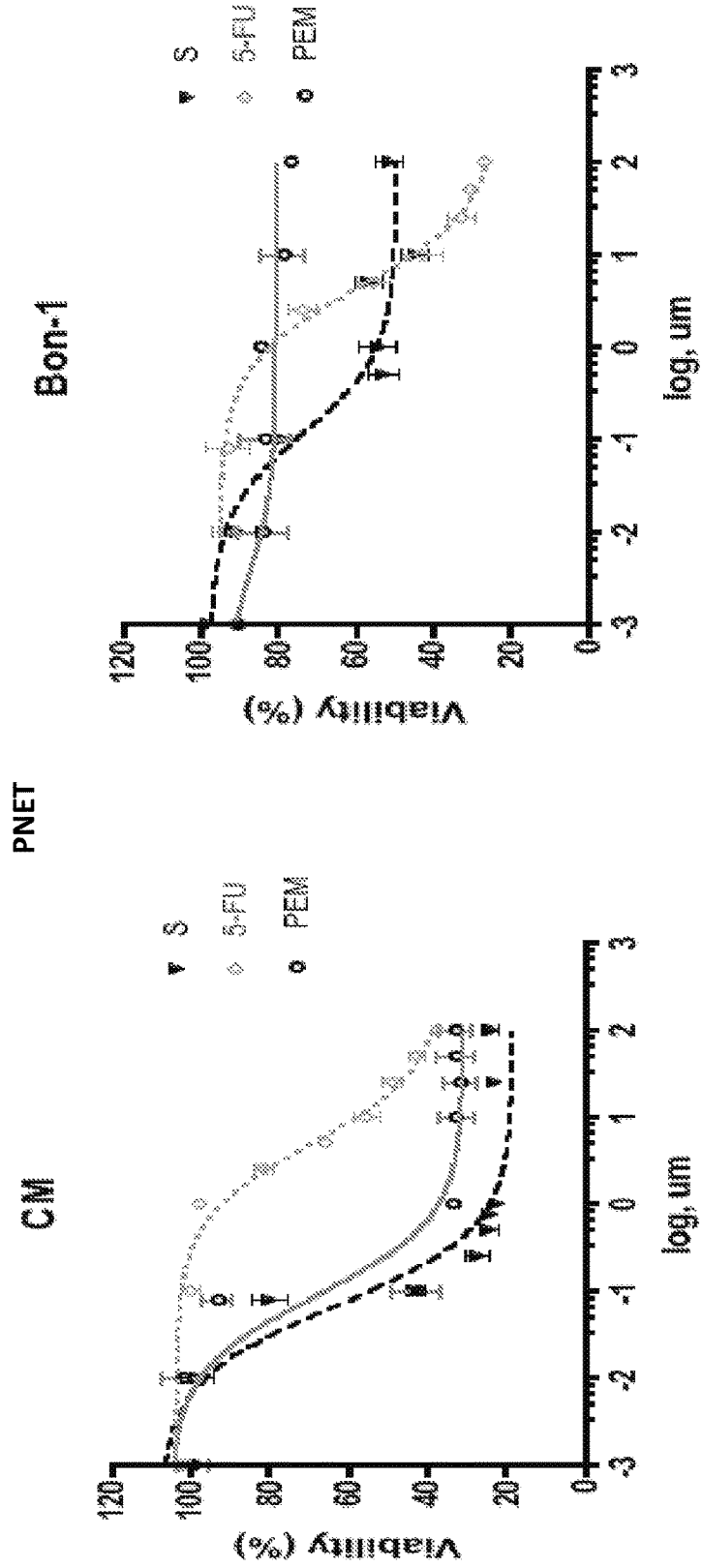
FIG. 11. Effect of compound S on growth inhibition of pancreatic neuroendocrine cell lines Bon1 and CM compared to pemetrexed and 5-FU FIG. 12. Dose-dependent growth inhibition of pancreatic ductal adenocarcinoma cell lines Panc-1 and Miapaca-2 by compounds S, U, P, G and M.
Figure 12:
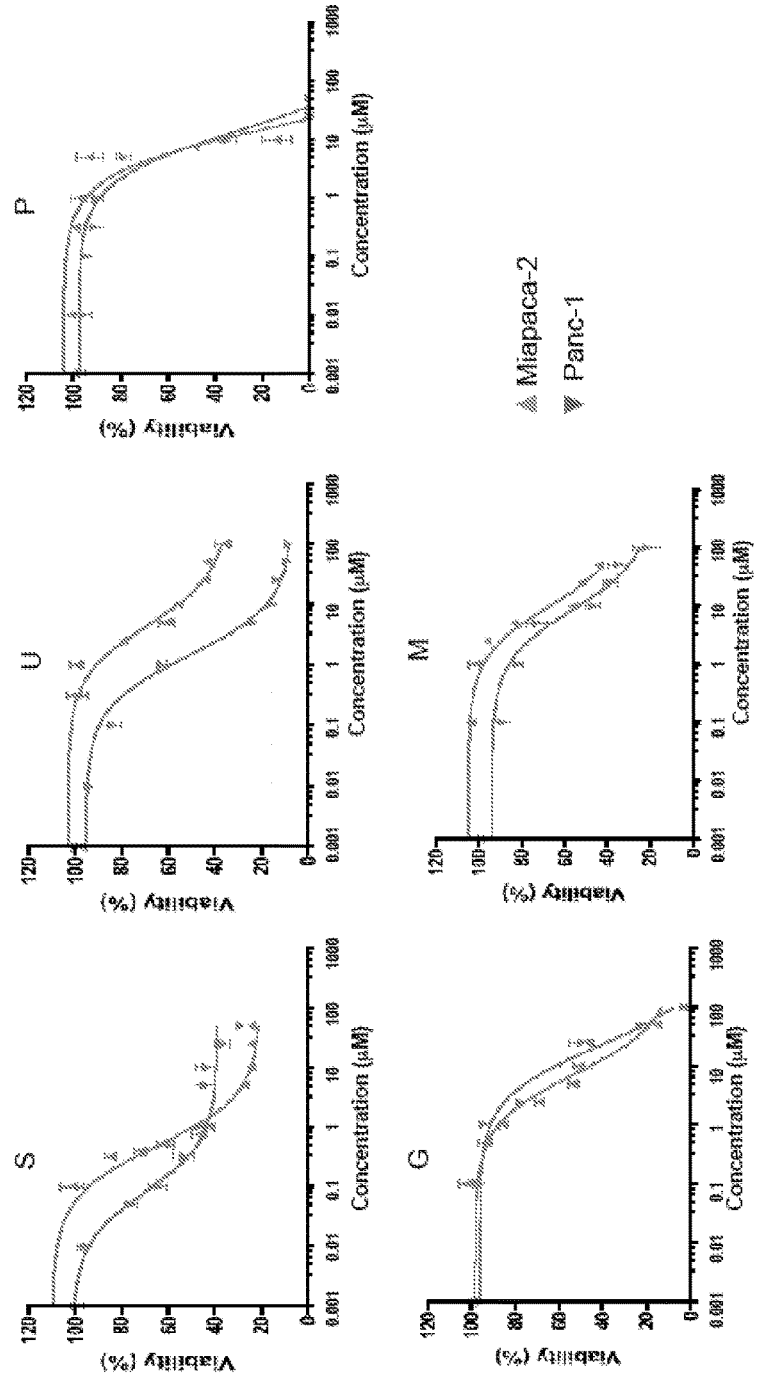
Figure 13:
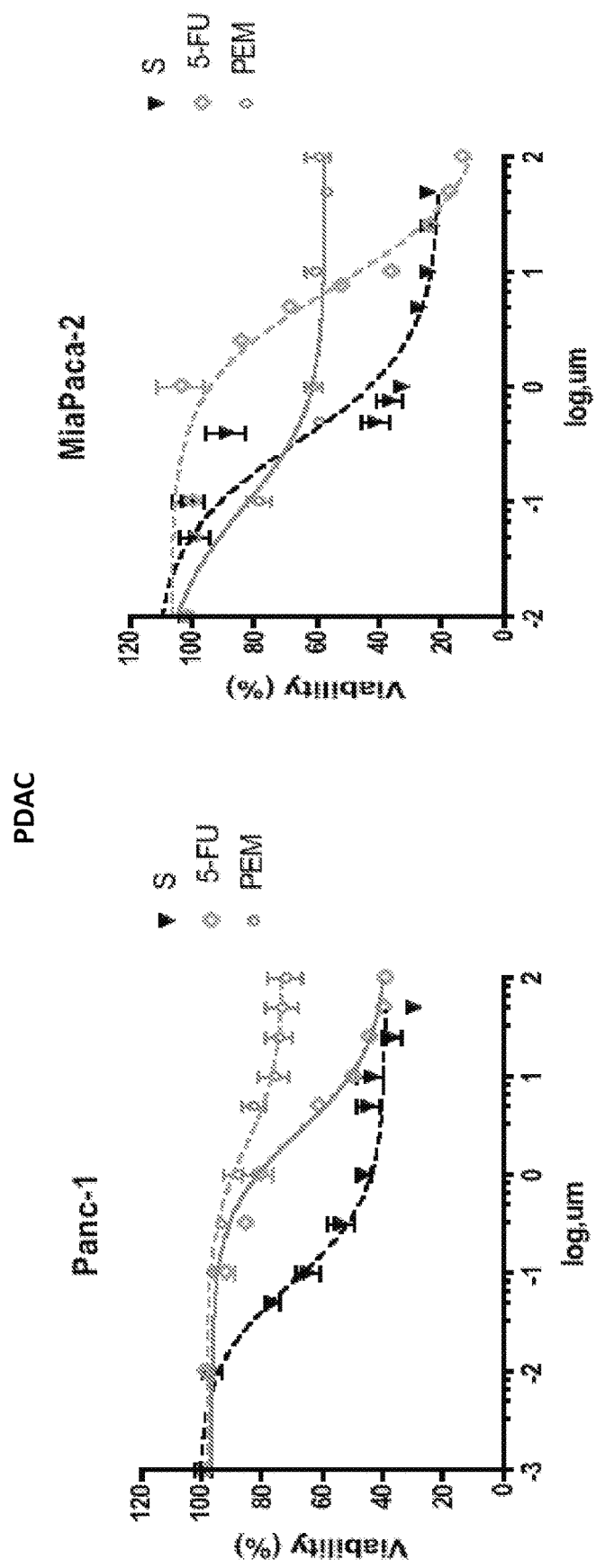
FIG. 13. Effect of compound S on growth inhibition of pancreatic ductal adenocarcinoma cell lines Panc-1 and Miapaca-2 compared to pemetrexed and 5-FU FIG. 14. Dose-dependent growth inhibition of mouse histiocytic sarcoma from genetically engineered mice with p16 deletion and activated hTS by compounds S, U and P.

Complete dose response relationships for five most promising compounds (P, U, S, M and G) have been established in pancreatic neuroendocrine cancer, pancreatic ductal cancer and small cell lung cancer cell lines (Table 3). In human small cell lung cancer cell lines H1607 and H1048 (FIGS. 8, 9), compounds S, M, P, U and G showed GI50' values in the range of 0.09-29 µM. In pancreatic ductal adenocarcinoma cell lines Miapaca-2 and Panc-1—GI50 values were between 0.5-24 µM (FIGS. 12, 13). In pancreatic neuroendocrine tumors Bon1 and CM—the range was larger with GI50 values within 0.1-100 µM (FIGS. 10, 11). Such discrepancy in response to drugs between Bon1 and CM cells can be explained at least in part by different tumor type of these cells. CM cells were derived from insulinoma, a typical beta cell tumor that secrets insulin while Bon cells are carcinoid tumors derived from lymph nodes that produce serotonin. Compound S demonstrated good efficacy in all tested cell types (with exception of Bon1 cells, GI50=100 µM) and showed strongest sensitivity in H1048 (SCLC) and CM (insulinoma) cell lines with GI50 values of 96 and 93 nM, respectively.

Figure 14:
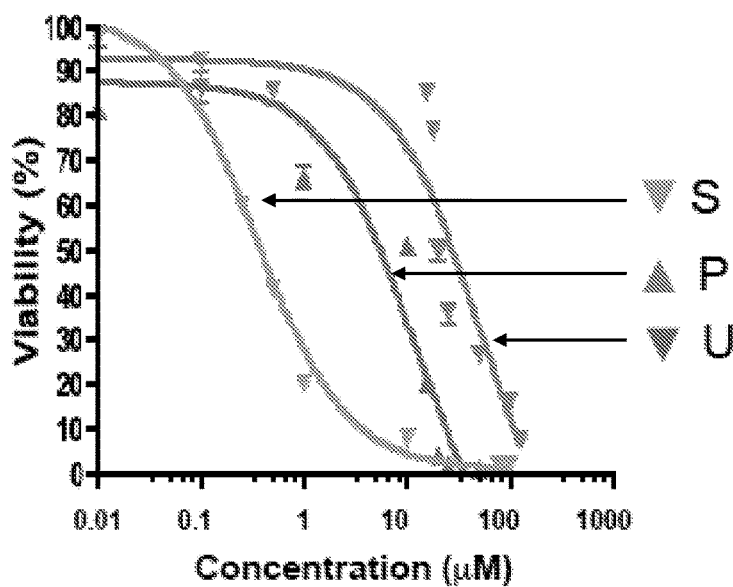

[1] GI50 here is referred to a concentration of a compound needed to achieve 50% growth inhibition We also tested the compounds S, U and P in mouse histiocytic sarcoma cell line that was derived from genetically engineered mouse model with p16 deletion and activated hTS overexpression. All three of the compounds showed strong growth inhibition with GI50 values from 0.4-20 µM (FIG. 14). The most potent anti-proliferative compound overall—compound S decreased cell viability in a dose-dependent manner and demonstrated up to 169-fold lower GI50 than 5-FU and up to 416-fold lower GI50 than pemetrexed. Dose-response curves and GI50 values for all compounds tested can be found in Table 3 and FIGS. 8-13.

The compounds of the current invention were designed to target TS through a completely different mechanism than 5-FU. Examples of six of the newly identified TS inhibitors that inhibit cancer cell growth are presented below. These six representative compounds were shown to selectively target TS in vitro and significantly reduce cell viability of human cancer cell lines in vivo.

Figure 15:
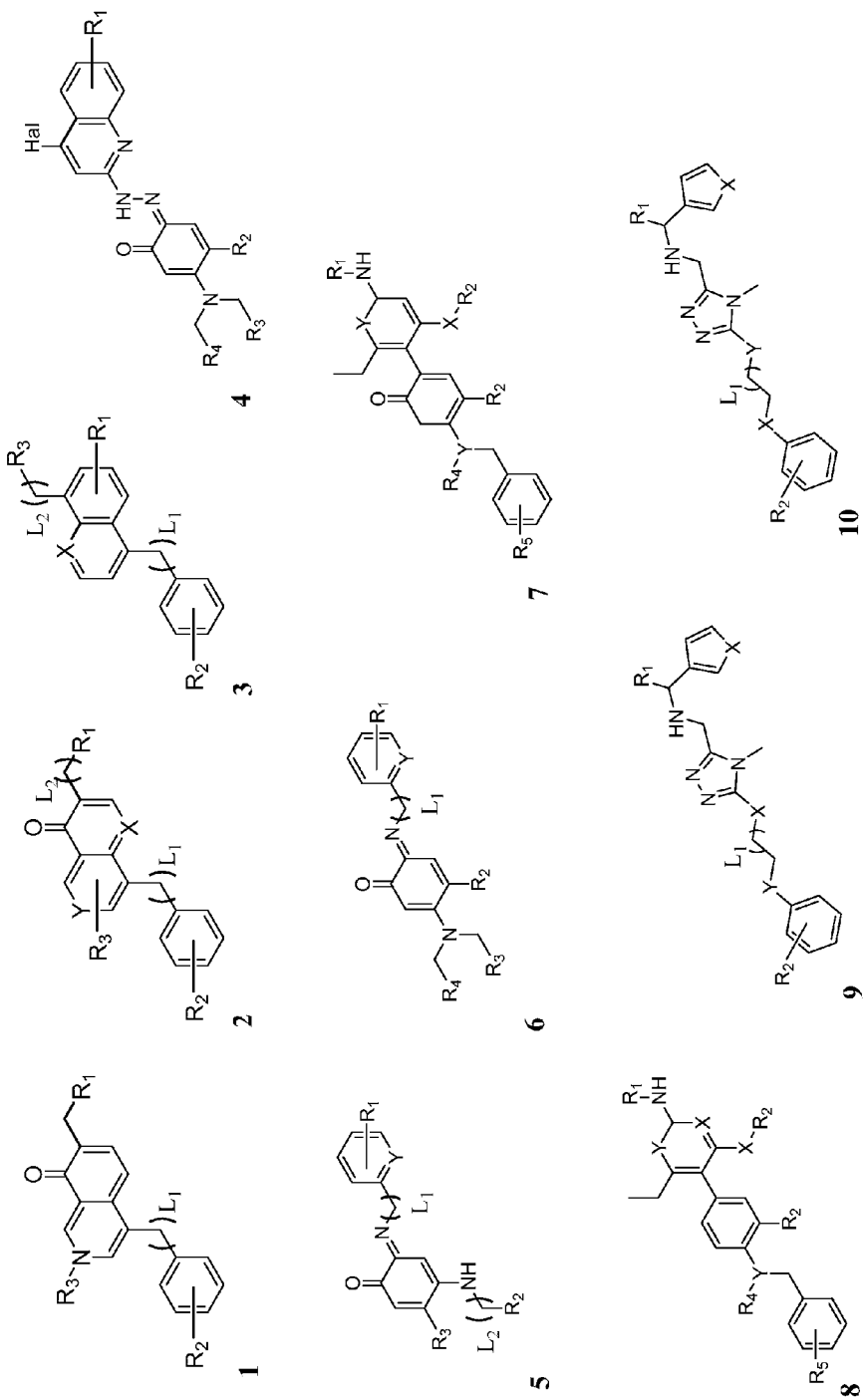
FIG. 15. Novel Thymidylate synthase inhibitors presented by general formulae (structures 1-10), where R1, R2, R3, R4, R5 as well as L1, L2, X, Y and Hal represent various substituent groups that are described in detail below. In all structures shown in FIG. 23, R represents a substituent group, where R1, R3, R4 and R5 represent hydrogen atom, methyl group or amino, nitro, amidino, sulpho, sulphonamido, carboxy, cyano group. R1, R3, R4 and R5 can also represent aromatic, heteroaromatic or heterocyclic substituent group such as phenyl, thienyl, pyrril, pyrazolyl, imidazolyl, isoxazyl, triazolyl, tetrazolyl, thiazolyl, oxazolyl, quinazolyl, pyridyl, pyrimidyl group. R1, R3, R4 and R5 can also represent straight chain or branched lower alkyl, alkenyl, alkylamino, hydroxyalkyl group, or carbonyl, cyclopropyl or trifluoromethyl group. In all examples shown above, R2 represents hydrogen atom, methyl group or hydroxy, amino, nitro, sulpho, sulphonamido, carboxy, cyano group. X represents carbon, nitrogen, oxygen or sulphur atom at the indicated position, producing respective alkyl, alkylamino, alkoxy, sulphaalkyl derivatives. Y represents carbon, nitrogen or oxygen atom at the indicated position, producing respective alkyl, alkylamino, alkoxy, sulphaalkyl derivative. Hal represents a halogen group producing respective fluoro, chloro, bromo, and iodo-substituted derivatives. L1 and L2 represent linkage bridging the two carbons at the specified position surrounded by parentheses and may include lower unbranched alkyl, alkenyl, amidino or ureido type of linkage. In all examples shown above, substituent group position is as specified. R-group pointed within the aromatic ring denotes that any of the positions at the ring can be substituted within respective R-group. In some cases up to five different aromatic carbons can carry respective substituent group.

The current invention also discloses examples of the scaffolds that represent second generation small molecule inhibitors of TS (FIG. 15).

Maximal Tolerated Dose Study

To establish the maximum tolerated dose (MTD) for most promising new inhibitors, both immunodeficient SCID and immunocompetent FVB.129 mice were treated daily with compound S and methylated version of compound S at 12.5, 50, and 100 MKG (mg/kg) by i.p. injection (Tables 4 and 5). SCID immunodeficient mice were i.p. injected daily for 3 weeks and kept under observation for one additional week. Animals' weights were measured daily and the data is presented as the percentage of weight change from day 1 of treatment to day 28 at the termination of the experiment (Table 4). FVB.129 immunocompetent mice were i.p. injected daily for 2 weeks and kept under observation for one additional week. Animals' weights were measure daily and the data is presented as the percentage of weight change from day 1 of treatment to day 21 at the termination of the experiment (Table 5).

In SCID mice, both compound S and methylated derivative of compound S were well tolerated with MTD ≥100 mg/kg for methylated derivative and MTD ≥50 mg/kg for unmodified compound S (Tables 4 and 5).

In FVB.129 mice, only the methylated derivative of compound S was well tolerated and animals appeared healthy when treated with up to 100 mg/kg of compound. FVB.129 animals treated with original compound S did not tolerate the compound and died at 50 MKG at day 6 after treatment. Thus, we have established the maximal tolerated doses for both compounds and identified a derivative of compound S that is less toxic to immunocompetent FVB.129 mice.

TABLE 1

Compound structures of the novel allosteric inhibitors of TS

| | Compound structure | NSC number | Chemical name |
|---|---|---|---|
| 1 | 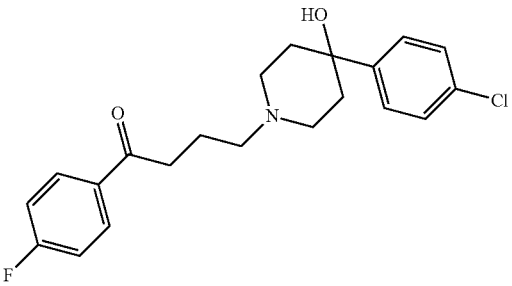 [SMILES: O=C(CCCN1CCC(O)(c2ccc(Cl)cc2)CC1)c1ccc(F)cc1] N 615296 | NSC 615296 | 4-(4-(4-chlorophenyl)-4-hydroxypiperidin-1-yl)-1-(4-fluorophenyl)butan-1-one |

TABLE 1-continued

Compound structures of the novel allosteric inhibitors of TS

| | Compound structure | NSC number | Chemical name |
|---|---|---|---|
| 2 | 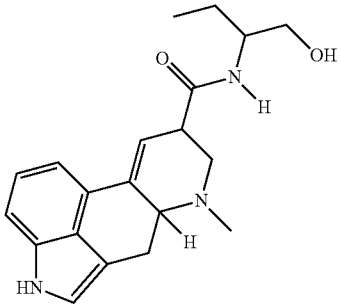 [SMILES: CCC(CO)NC(=O)C1C=C2c3cccc4[nH]cc(c34)CC2N(C)C1]<br>O 186067 | NSC 186067 | N-(1-hydroxybutan-2-yl)-7-methyl-4,6,6a,7,8,9-hexahydroindolo[4,3-fg]quinoline-9-carboxamide |
| 3 | 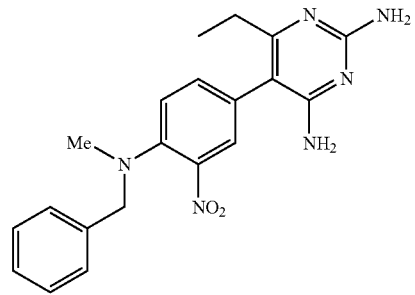 [SMILES: CCc1nc(N)nc(N)c1-c1ccc(N(C)Cc2ccccc2)c([N+](=O)[O-])c1]<br>S 382035 | NSC 382035 | 5-[4-[benzyl(methyl)amino]-3-nitrophenyl]-6-ethylpyrimidine-2,4-diamine |
| 4 | 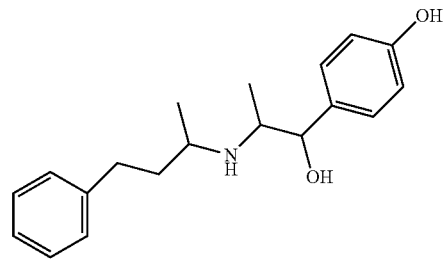 [SMILES: CC(CCc1ccccc1)NC(C)C(O)c1ccc(O)cc1]<br>Q 142004 | NSC 142004 | 4-(1-hydroxy-2-((4-phenylbutan-2-yl)amino)propyl)phenol |
| 5 | 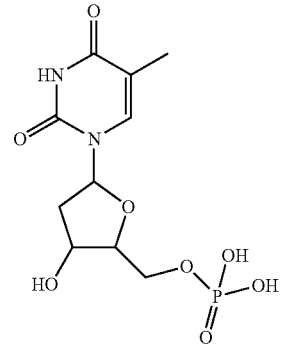 [SMILES: Cc1cn(C2CC(O)C(COP(=O)(O)O)O2)c(=O)[nH]c1=O]<br>W 46713 | NSC 46713 | (3-hydroxy-5-(5-methyl-2,4-dioxo-3,4-dihydropyrimidin-1(2H)-yl)tetrahydrofuran-2-yl)methyl dihydrogen phosphate |

TABLE 1-continued

Compound structures of the novel allosteric inhibitors of TS

| | Compound structure | NSC number | Chemical name |
|---|---|---|---|
| 6 | 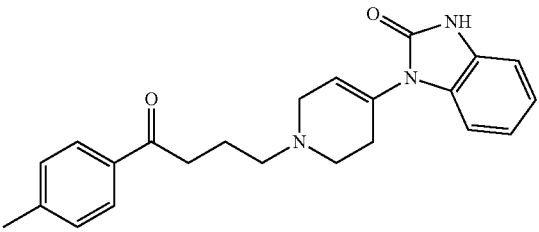 [SMILES: Cc1ccc(C(=O)CCCN2CC=C(n3c(=O)[nH]c4ccccc43)CC2)cc1]<br>R 169874 | NSC 169874 | 1-(1-(4-oxo-4-(p-tolyl)butyl)-1,2,3,6-tetrahydropyridin-4-yl)-1H-benzo[d]imidazol-2(3H)-one |
| 7 | 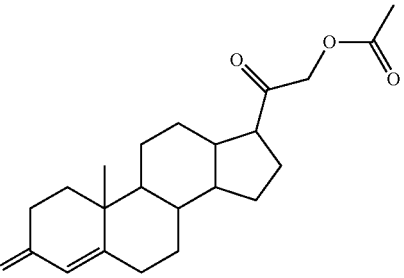<br>V 9567 | NSC 9667 | 2-(10-methyl-3-oxo-2,3,6,7,8,9,10,11,12,13,14,15,16,17-tetradecahydro-1H-cyclopenta[a]phenanthren-17-yl)-2-oxoethyl acetate |
| 8 | 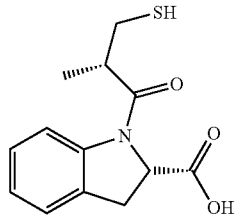<br>T 604536 | NSC 604536 | (S)-1-((S)-3-mercapto-2-methylpropanoyl)indoline-2-carboxylic acid |
| 9 | 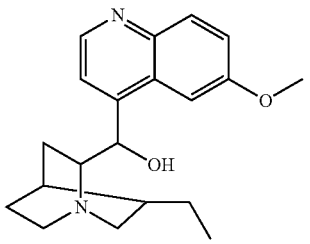 [SMILES: CCC1CN2CCC1CC2C(O)c1ccnc2ccc(OC)cc12]<br>A 41799 | NSC 41799 | ((1S)-5-ethylquinuclidin-2-yl)(6-methoxyquinolin-4-yl) methanol |
| 10 | 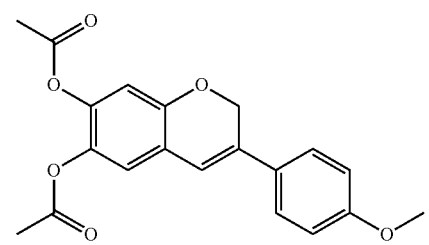 [SMILES: COc1ccc(C2=Cc3cc(OC(C)=O)c(OC(C)=O)cc3OC2)cc1]<br>B 600287 | NSC 600287 | 3-(4-methoxyphenyl)-2H-chromene-6,7-diyl diacetate |

TABLE 1-continued

Compound structures of the novel allosteric inhibitors of TS

| | Compound structure | NSC number | Chemical name |
|---|---|---|---|
| 11 | D 625487 | NSC 625487 | 1-(2,6-difluorophenyl)-1,3-dihydrobenzo[4,5]imidazo[1,2-c]thiazole |
| 12 | C 170982 | NSC 170982 | 1-(1-(4-(4-fluorophenyl)-4-oxobutyl)piperidin-4-yl)-1H-benzo[d]imidazol-2(3H)-one |
| 13 | F 169873 | NSC 169873 | 1-(1-(4-(4-fluorophenyl)-4-oxobutyl)piperidin-4-yl)-1H-benzo[d]imidazol-2(3H)-one |
| 14 | I 304398 | NSC 304398 | 1-(3-(4-(3-chlorophenyl)piperazin-1-yl)propyl)-3,4-diethyl-1H-1,2,4-triazol-5(4H)-one |
| 15 | E 299589 | NSC 299589 | 5-chloro-1-(1-(3-(2-oxo-2,3-dihydro-1H-benzo[d]imidazol-1-yl)propyl)piperidin-4-yl)-1H-benzo[d]imidazol-2(3H)-one |

TABLE 1-continued

Compound structures of the novel allosteric inhibitors of TS

| | Compound structure | NSC number | Chemical name |
|---|---|---|---|
| 16 | 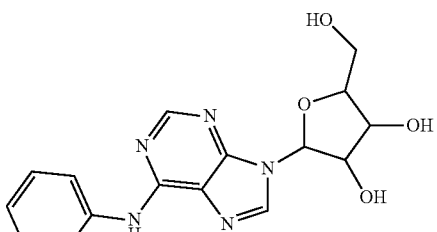<br>K 337772 | NSC 337772 | 2-(hydroxymethyl)-5-(6-(phenylamino)-9H-purin-9-yl)tetrahydrofuran-3,4-diol |
| 18 | 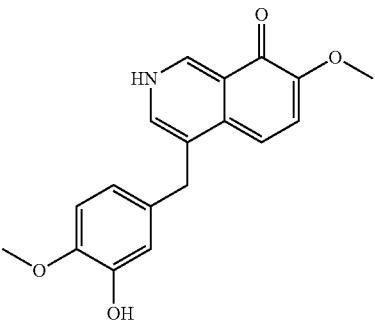<br>M 131747 | NSC 131747 | 4-(3-hydroxy-4-methoxybenzyl)-7-methoxyisoquinolin-8(2H)-one |
| 19 | 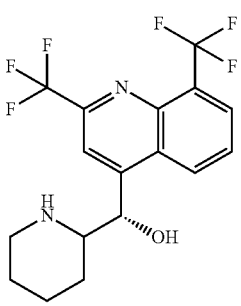 [SMILES: O[C@@H](c1cc(C(F)(F)F)nc2c(C(F)(F)F)cccc12)C1CCCCN1]<br>P 157387 | NSC 157387 | (1S)-(2,8-bis(trifluoromethyl)quinolin-4-yl)(piperidin-2-yl)methanol |
| 20 | 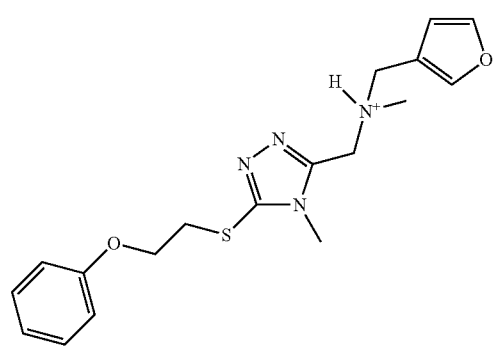 [SMILES: Cn1c(C[NH+](C)Cc2ccoc2)nnc1SCCOc1ccccc1]<br>G 609874 | NSC 609874 | 1-(furan-3-yl)-N-methyl-N-((4-methyl-5-((2-phenoxyethyl)thio)-4H-1,2,4-triazol-3-yl)methyl)methanaminium |

TABLE 1-continued

Compound structures of the novel allosteric inhibitors of TS

| | Compound structure | NSC number | Chemical name |
|---|---|---|---|
| 21 | U 367081 | NSC 367081 | (E)-6-(2-(4-bromopyridin-2-yl)hydrazono)-3-(diethylamino)cyclohexa-2,4-dienone |
| 22 | J 612049 | NSC 612049 | 9-((2S,5R)-5-(hydroxymethyl)tetrahydrofuran-2-yl)-3H-purin-6(9H)-one |

TABLE 2

Novel allosteric inhibitors of TS inhibiting growth of multiple human cancer cell lines

| Compound structure | NSC number | Chemical name |
|---|---|---|
| M 131747 | NSC 131747 | 4-(3-hydroxy-4-methoxybenzyl)-7-methoxyisoquinolin-8(2H)-one |

TABLE 2-continued

Novel allosteric inhibitors of TS inhibiting growth of multiple human cancer cell lines

| Compound structure | NSC number | Chemical name |
|---|---|---|
| P 157387 | NSC 157387 | (1S)-(2,8-bis(trifluoromethyl)quinolin-4-yl)(piperidin-2-yl)methanol |
| J 612049 | NSC 612049 | 9-((2S,5R)-5-(hydroxymethyl)tetrahydrofuran-2-yl)-3H-purin-6(9H)-one |
| S 382035 | NSC 382035 | 5-[4-[benzyl(methyl)amino]-3-nitrophenyl]-6-ethylpyrimidine-2,4-diamine |
| U 367081 | NSC 367081 | (E)-6-(2-(4-bromopyridin-2-yl)hydrazono)-3-(diethylamino)cyclohexa-2,4-dienone |

TABLE 2-continued

Novel allosteric inhibitors of TS inhibiting growth of multiple human cancer cell lines

| Compound structure | NSC number | Chemical name |
|---|---|---|
| 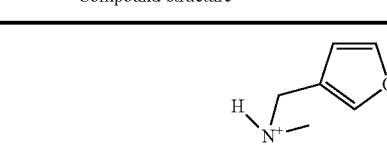<br>G 609874 | NSC 609874 | 1-(furan-3-yl)-N-methyl-N-((4-methyl-5-((2-phenoxyethyl)thio)-4H-1,2,4-triazol-3-yl)methyl)methanaminium |

TABLE 3

Compound GI50 values in small cell lung cancer (SCLC), pancreatic neuroendocrine tumors (PNET) and pancreatic adenocarcinoma (PDAC)

| | SCLC | | PNET | | PDAC | | mHS* |
|---|---|---|---|---|---|---|---|
| Compound | H1607 | H1048 | CM | Bon-1 | MiaPaca-2 | Panc-1 | 5278mHS |
| P 157387 | 8.6E−06 | 1.6E−05 | 1.6E−05 | 7.6E−06 | 7.0E−06 | 8.4E−06 | 2.3E−06 |
| U 367081 | 2.5E−06 | 3.1E−06 | 1.3E−05 | 2.4E−06 | 1.2E−05 | 1.3E−06 | 2.1E−05 |
| S 382035 | 8.2E−06 | 9.6E−08 | 9.3E−08 | 1.0E−04 | 4.8E−07 | 9.3E−07 | 4.2E−07 |
| M 131747 | 2.6E−06 | 1.6E−05 | 2.9E−05 | 2.6E−05 | 2.4E−05 | 1.5E−05 | |
| G 609874 | 2.9E−05 | 4.3E−06 | 3.2E−05 | 3.9E−07 | 9.7E−06 | 1.5E−05 | |
| 5-FU | 3.6E−05 | 2.3E−06 | 1.6E−05 | 7.6E−06 | 8.1E−06 | 1.1E−05 | |
| Pemetrexed | >2.0E−04 | 1.3E−07 | 8.7E−08 | >2.0E−04 | >2.0E−04 | >2.0E−04 | |

*mouse histiocytic sarcoma-(mHS)

TABLE 4

MTD study for compound S and methylated compound S in SCID mice.

| Compound | MKG* | # of mice | Percentage of weight change (%) | | | | | | | | | | | | | |
|---|---|---|---|---|---|---|---|---|---|---|---|---|---|---|---|---|
| | | | D1 | D2 | D3 | D4 | D5 | D6 | D7 | D8 | D9 | D10 | D11 | D12 | D13 | D14 |
| methylated derivative of compound S | 12.5 | 1 | 100 | 106 | 111 | 106 | 111 | 112 | 114 | 114 | 112 | 112 | 110 | 111 | 112 | 114 |
| | | 2 | 100 | 108 | 116 | 118 | 119 | 123 | 127 | 127 | 128 | 131 | 133 | 133 | 130 | 131 |
| | | 3 | 100 | 112 | 115 | 118 | 118 | 123 | 126 | 123 | 123 | 126 | 128 | 128 | 129 | 115 |
| | | Mean | 100 | 109 | 114 | 114 | 116 | 120 | 122 | 121 | 121 | 123 | 124 | 124 | 124 | 120 |
| | 25 | 1 | 100 | 104 | 104 | 106 | 111 | 112 | 113 | 111 | 115 | 116 | 112 | 113 | 114 | 111 |
| | | 2 | 100 | 102 | 104 | 106 | 110 | 113 | 119 | 117 | 118 | 120 | 123 | 124 | 130 | 127 |
| | | 3 | 100 | 117 | 114 | 117 | 121 | 125 | 130 | 133 | 135 | 135 | 135 | 135 | 137 | 157 |
| | | Mean | 100 | 108 | 107 | 110 | 114 | 117 | 121 | 120 | 122 | 124 | 123 | 124 | 127 | 132 |
| | 50 | 1 | 100 | 102 | 104 | 105 | 105 | 106 | 110 | 109 | 111 | 110 | 109 | 109 | 110 | 112 |
| | | 2 | 100 | 104 | 110 | 109 | 112 | 112 | 115 | 113 | 110 | 113 | 116 | 117 | 117 | 125 |
| | | 3 | 100 | 106 | 109 | 111 | 117 | 118 | 121 | 122 | 127 | 127 | 127 | 127 | 128 | 132 |
| | | Mean | 100 | 104 | 108 | 108 | 111 | 112 | 115 | 115 | 116 | 117 | 117 | 118 | 118 | 123 |
| | 100 | 1 | 100 | 102 | 102 | 100 | 102 | 105 | 110 | 114 | 105 | 105 | 103 | 104 | 108 | 109 |
| | | 2 | 100 | 100 | 98 | 98 | 101 | 105 | 106 | 105 | 104 | 105 | 108 | 113 | 114 | 116 |
| | | 3 | 100 | 106 | 106 | 104 | 104 | 110 | 121 | 117 | FDN | | | | | |
| | | Mean | 100 | 102 | 102 | 101 | 102 | 106 | 112 | 112 | 105 | 105 | 105 | 108 | 111 | 112 |
| compound S | 50 | 1 | 100 | 107 | 125 | 122 | 126 | 129 | 131 | 125 | 126 | 128 | 133 | 134 | 135 | 135 |
| | | 2 | 100 | 109 | 130 | 127 | 131 | 132 | 136 | 137 | 133 | 134 | 140 | 142 | 143 | 144 |
| | | Mean | 100 | 108 | 127 | 125 | 129 | 130 | 133 | 131 | 130 | 131 | 137 | 138 | 139 | 140 |
| | 100 | 1 | 100 | FDN | | | | | | | | | | | | |
| | | 2 | 100 | FDN | | | | | | | | | | | | |
| | | Mean | 100 | 0 | | | | | | | | | | | | |

TABLE 4-continued

MTD study for compound S and methylated compound S in SCID mice.

| Compound | MKG * | # of mice | Percentage of weight change (%) | | | | | | | | | | | | | |
|---|---|---|---|---|---|---|---|---|---|---|---|---|---|---|---|---|
| | | | D15 | D16 | D17 | D18 | D19 | D20 | D21 | D22 | D23 | D24 | D25 | D26 | D27 | D28 |
| methylated derivative of compound S | 12.5 | 1 | 115 | 115 | 117 | 112 | 112 | 114 | 115 | 119 | 120 | 121 | 121 | 121 | 121 | 121 |
| | | 2 | 122 | 120 | 120 | 120 | 120 | 121 | 121 | 123 | 125 | 127 | 131 | 131 | 130 | 129 |
| | | 3 | 132 | 131 | 129 | 136 | 137 | 138 | 139 | 141 | 139 | 139 | 139 | 139 | 140 | 141 |
| | | Mean | 123 | 122 | 122 | 123 | 123 | 124 | 125 | 128 | 128 | 129 | 130 | 130 | 130 | 130 |
| | 25 | 1 | 115 | 118 | 118 | 116 | 116 | 118 | 120 | 122 | 120 | 122 | 120 | 122 | 122 | 123 |
| | | 2 | 130 | 128 | 129 | 134 | 134 | 134 | 135 | 138 | 140 | 140 | 143 | 143 | 143 | 143 |
| | | 3 | 142 | 140 | 141 | 141 | 143 | 143 | 144 | 151 | 153 | 154 | 157 | 157 | 157 | 157 |
| | | Mean | 129 | 129 | 129 | 130 | 131 | 132 | 133 | 137 | 138 | 139 | 140 | 141 | 141 | 141 |
| | 50 | 1 | 117 | 117 | 117 | 117 | 116 | 117 | 119 | 121 | 122 | 122 | 124 | 125 | 125 | 127 |
| | | 2 | 130 | 130 | 132 | 134 | 133 | 133 | 134 | 138 | 141 | 141 | 145 | 145 | 145 | 143 |
| | | 3 | 136 | 129 | 129 | 132 | 132 | 133 | 136 | 136 | 139 | 140 | 144 | 144 | 144 | 144 |
| | | Mean | 128 | 125 | 126 | 127 | 127 | 128 | 129 | 131 | 134 | 135 | 138 | 138 | 138 | 138 |
| | 100 | 1 | 108 | 109 | 111 | 117 | 120 | 124 | 130 | 132 | 132 | 133 | 133 | 133 | 135 | 138 |
| | | 2 | 116 | 116 | 118 | 120 | 121 | 124 | 125 | 125 | 125 | 125 | 127 | 129 | 129 | 132 |
| | | 3 | | | | | | | | | | | | | | |
| | | Mean | 112 | 112 | 114 | 118 | 120 | 124 | 127 | 128 | 129 | 129 | 130 | 131 | 132 | 135 |
| compound S | 50 | 1 | 138 | 138 | 138 | 137 | 138 | 137 | 137 | 137 | 137 | 138 | 138 | 138 | 138 | 140 |
| | | 2 | 146 | 146 | 147 | 148 | 148 | 148 | 148 | 148 | 148 | 146 | 146 | 146 | 145 | 148 |
| | | Mean | 142 | 142 | 142 | 142 | 143 | 143 | 142 | 143 | 142 | 142 | 142 | 142 | 141 | 144 |
| | 100 | 1 | | | | | | | | | | | | | | |
| | | 2 | | | | | | | | | | | | | | |
| | | Mean | | | | | | | | | | | | | | |

* i.p Daily for 21 days and watch one more week; FDN, animal found dead

TABLE 5

MTD study for compound S and methylated compound S in FVB.129 mice.

| Compound | MKG * | # of mice | Percentage of weight change (%) | | | | | | | | | | |
|---|---|---|---|---|---|---|---|---|---|---|---|---|---|
| | | | D1 | D2 | D3 | D4 | D5 | D6 | D7 | D8 | D9 | D10 | D11 |
| methylated derivative of compound S | 50 | 1 | 100 | 101 | 101 | 99 | 101 | 103 | 103 | 103 | 104 | 105 | 106 |
| | | 2 | 100 | 101 | 100 | 101 | 102 | 104 | 106 | 107 | 107 | 107 | 107 |
| | | 3 | 100 | 99 | 98 | 98 | 95 | 95 | 95 | 98 | 98 | 98 | 99 |
| | | Mean | 100 | 100 | 100 | 100 | 99 | 101 | 101 | 102 | 103 | 103 | 104 |
| | 100 | 1 | 100 | 101 | 100 | 100 | 101 | 103 | 105 | 102 | 102 | 102 | 103 |
| | | 2 | 100 | 100 | 99 | 102 | 106 | 106 | 110 | 105 | 105 | 106 | 106 |
| | | 3 | 100 | 101 | 101 | 101 | 101 | 101 | 101 | 104 | 105 | 107 | 108 |
| | | Mean | 100 | 100 | 100 | 101 | 103 | 103 | 105 | 104 | 104 | 105 | 106 |
| compound S | 50 | 1 | 100 | 99 | 101 | 101 | 101 | FDN | | | | | |
| | | 2 | 100 | 102 | 103 | 104 | 106 | FDN | | | | | |
| | | 3 | 100 | 100 | 98 | 99 | 98 | FDN | | | | | |
| | | Mean | 100 | 101 | 101 | 101 | 102 | | | | | | |
| | 100 | 1 | 100 | 100 | 99 | 99 | FDN | | | | | | |
| | | 2 | 100 | 101 | 100 | 100 | FDN | | | | | | |
| | | 3 | 100 | 100 | 101 | 102 | FDN | | | | | | |
| | | Mean | 100 | 100 | 100 | 100 | | | | | | | |

| Compound | MKG * | # of mice | Percentage of weight change (%) | | | | | | | | | |
|---|---|---|---|---|---|---|---|---|---|---|---|---|
| | | | D12 | D13 | D14 | D15 | D16 | D17 | D18 | D19 | D20 | D21 |
| methylated derivative of compound S | 50 | 1 | 107 | 107 | 107 | 107 | 108 | 108 | 108 | 107 | 108 | 108 |
| | | 2 | 108 | 107 | 107 | 107 | 107 | 107 | 107 | 107 | 107 | 107 |
| | | 3 | 99 | 100 | 100 | 100 | 100 | 100 | 100 | 100 | 100 | 100 |
| | | Mean | 105 | 105 | 105 | 105 | 105 | 105 | 105 | 105 | 105 | 105 |
| | 100 | 1 | 101 | 98 | 98 | 88 | FDN | | | | | |
| | | 2 | 107 | 103 | 103 | 104 | 104 | 104 | 104 | 104 | 104 | 104 |
| | | 3 | 109 | 108 | 109 | 109 | 108 | 109 | 109 | 109 | 108 | 109 |
| | | Mean | 106 | 103 | 103 | 100 | 106 | 107 | 107 | 106 | 106 | 107 |
| compound S | 50 | 1 | | | | | | | | | | |
| | | 2 | | | | | | | | | | |
| | | 3 | | | | | | | | | | |
| | | Mean | | | | | | | | | | |
| | 100 | 1 | | | | | | | | | | |
| | | 2 | | | | | | | | | | |
| | | 3 | | | | | | | | | | |
| | | Mean | | | | | | | | | | |

* i.p Daily for 14 days and watch one more week; FDN, animal found dead;

Certain other aspects of the invention provide pharmaceutical compositions comprising one or more of the compounds disclosed herein and a pharmaceutically acceptable carrier and/or excipient, optionally in combination with chemotherapeutic agent. Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents (e.g., a Thymidylate synthase inhibitor as disclosed herein alone or in combination with a chemotherapeutic agent) substantially immediately upon administration or at any predetermined time or time period after administration.

Compositions for parenteral administration are generally physiologically compatible sterile solutions or suspensions which can optionally be prepared immediately before use from solid or lyophilized form. Adjuvants such as a local anesthetic, preservative and buffering agents can be dissolved in the vehicle and a surfactant or wetting agent can be included in the composition to facilitate uniform distribution of the active ingredient.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

A number of terms and phrases are defined below.

The singular forms "a", "an", and "the" include plural forms unless the context clearly dictates otherwise. Additionally, as used herein, the terms "comprises," "comprising," "containing," "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "cancer" and "cancerous" refer to or describe the physiological condition in mammals, in which a population of cells are characterized by unregulated cell growth. Examples of cancer include, but are not limited to, carcinoma, lymphoma, blastoma, sarcoma, and leukemia. Non-limiting examples of such cancers include squamous cell cancer, small-cell lung cancer, non-small cell lung cancer, adenocarcinoma of the lung, squamous carcinoma of the lung, lung cancer, leukemia, cancer of the peritoneum, hepatocellular cancer, gastrointestinal cancer, pancreatic cancer, glioblastoma (i.e., brain cancer), CNS cancer, cervical cancer, ovarian cancer, liver cancer, bladder cancer, hepatoma, breast cancer, colon cancer, colorectal cancer, endometrial or uterine carcinoma, salivary gland carcinoma, kidney/renal cancer, liver cancer, melanoma, prostate cancer, vulval cancer, thyroid cancer, hepatic carcinoma, acute lymphoblatic leukemia (ALL), acute myelogenous leukemia (AML), acute promyelocytic leukemia, chronic lymphocytic leukemia (CLL), chronic myelogenous leukemia (CML), acute monocytic leukemia (AMOL), hairy cell leukemia, large cell immunoblastic lymphoma, plasmacytoma, multiple myeloma, Hodgkin's lymphoma, non-Hodgkin's lymphoma, and various types of head and neck cancer. In certain embodiments, methods of treating triple negative breast cancer (TNBC) are provided.

The terms "proliferative disorder" and "proliferative disease" refer to disorders associated with abnormal cell proliferation, such as cancer or dysplasia.

The term "tumor" as used herein refers to any mass of tissue that results from excessive cell growth or proliferation, either benign (noncancerous) or malignant (cancerous) including precancerous lesions.

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The term "inhibit tumor growth" and its grammatical equivalents refer to any mechanism by which tumor cell growth can be inhibited. In certain embodiments, tumor cell growth is inhibited by slowing proliferation of tumor cells. In certain embodiments, tumor cell growth is inhibited by halting proliferation of tumor cells. In certain embodiments, tumor cell growth is inhibited by killing tumor cells. In certain embodiments, tumor cell growth is inhibited by inducing apoptosis of tumor cells. In certain embodiments, tumor cell growth is inhibited by preventing migration of tumor cells. In certain embodiments, tumor cell growth is inhibited by preventing invasion of tumor cells.

The term "Thymidylate synthase inhibitor" refers to a compound disclosed in this application or an analog or a derivative thereof that inhibits the activity of thymidylate synthase as measured by an inhibition assay that is well-known in the art, including the 5,10-methylene tetrahydrofolate based spectrophotometric assay described herein.

The term "radiation therapy," "radiotherapeutic treatment," or "radiotherapy" is a term commonly used in the art to refer to multiple types of radiation therapy including internal and external radiation therapy, radioimmunotherapy, and the use of various types of radiation including X-rays, gamma rays, alpha particles, beta particles, photons, electrons, neutrons, radioisotopes, and other forms of ionizing radiation. Preferably, the radiotherapy involves the use of X-rays.

The methods and pharmaceutical composition of the invention can further utilize a chemotherapeutic agent suitable for the treatment of cancers, tumors and/or neoplasias. The "chemotherapeutic agent" may be selected from the group consisting of anthracyclines, platinum-based chemotherapy drugs, pyrimidine analogues, biologics (e.g., rituximab or other therapeutic monoclonal antibodies or cytokines), kinase inhibitors and alkylating agents, and combinations thereof. Anthracyclines may include, but are not limited to, doxorubicin, epirubicin, daunorubicin, aclarubicin, idarubicin, amrubicin, pirarubicin, valrubicin, zorubicin, carminomycin and detorubicin. Platinum-based chemotherapy drugs may include, but are not limited to, carboplatin, cisplatin, nedaplatin, oxaliplatin, triplatin tetranitrate and satraplatin. Pyrimidine analogues may include, but are not limited to, 5-Fluorouracil (5-FU), cytarabine and floxuridine. Alkylating agents may include, but are not limited to, nitrogen mustards such as cyclophosphamide, chlorambucil, uramustine, ifosfamide, melphalan and bendamustine; nitrosourea compounds such as carmustine, lomustine, semustine and streptozotocin; busulfan; dacarbazine; procarbazine; altretamine; mitozolomide; and temozolomide. Kinase inhibitors that can be used in this aspect of the invention include, and are not limited to, sorafenib, sunitinib and imatinib.

Terms such as "treating," "treatment," "to treat," "alleviating," and "to alleviate" refer to both 1) therapeutic measures that cure, slow down, lessen symptoms of, and/or halt progression of a diagnosed pathologic condition or proliferative disorder, and 2) prophylactic or preventative measures that prevent or slow the development of a targeted pathologic condition or proliferative disorder. Thus, those in need of treatment include those already with the proliferative disorder; those prone to having the proliferative disorder; and those in whom the proliferative disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs, including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life. By "ameliorate" is meant decrease, suppress, attenuate, diminish, arrest, or stabilize the development or progression of a disease or a symptom thereof.

The term "administering" is defined herein as a means of providing an agent or a composition containing the agent to a subject in a manner that results in the agent being inside the subject's body. Such an administration can be by any route including, without limitation, oral, subcutaneous, intradermal, intravenous, intra-arterial, intratumoral, intraperitoneal, and intramuscular.

The term "subject" or "patient" refers to an animal which is the object of treatment, observation, or experiment. By way of example only, a subject includes, but is not limited to, a mammal, including, but not limited to, a human or a non-human mammal, such as a bovine, equine, canine, ovine, murine or feline. In certain embodiments, the treatment of humans is contemplated by this invention.

The term "effective amount" means the amount of an agent required to ameliorate the symptoms of a disease relative to an untreated patient or to produce some desired therapeutic effect. The effective amount of active compound(s) used to practice the present invention for prevention or treatment of a disease varies depending upon the manner of administration, the age, body weight, and general health of the subject. Ultimately, the attending physician or veterinarian will decide the appropriate amount and dosage regimen.

The term "analog" means a molecule that is not identical, but has analogous functional or structural features. For example, an amide, ester, carbamate, carbonate, ureide, or phosphate analog of a compound is a molecule that either: 1) does not destroy the biological activity of the compound and confers upon that compound advantageous properties in vivo, such as uptake, duration of action, or onset of action; or 2) is itself biologically inactive but is converted in vivo to a biologically active compound.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Following examples illustrate procedures for practicing the invention. These examples should not be construed as limiting. All percentages are by weight and all solvent mixture proportions are by volume unless otherwise noted.

Example 1: Molecular Docking Studies

We have been able to identify a site at the dimer interface specific to inactive conformation of TS that is critical to TS enzymatic function. TS conformation with high asymmetry between the subunits (PDBID:1HVY) was selected as receptor target for molecular docking Protein structure was prepared by removing the heteroatoms and liganded molecules, energy minimizing in UCSF Chimera 1.5.2 and testing resulting geometries in Coot 0.6.2. National Cancer Institute (NCI) small molecule library of 139,735 compounds was extracted from ZINC and pruned to remove redundant structures and molecules with molecular weight less than 200 Da. Resulting compound library was docked (DOCK6.4) [28] [29] into selected structural pocket in 1000 orientations with flexible bond parameters enabled. To minimize noise, the compounds were selected based on averages obtained over 3 independent docking runs using different random seeds [30]. The top 1000 hits were re-scored using AMBER10 and visualized in PyMOL to check for consistency and geometric fit. 837 out of 1000 molecules were further selected and re-ranked based on predicted physicochemical characteristics (cLogP, pKa, solubility, etc.).

Example 2: Thymidylate Synthase Purification

Recombinant human Thymidylate synthase was purified according to published protocol [31]. Briefly, 5 mL of overnight *E. coli* M15 culture transformed with a vector carrying His-tagged recombinant human TS was inoculated with one liter of Luria-Bertrani broth, containing 100 µg/mol of ampicillin, and was left growing in shaking incubator at 37° C. for 4.5 hours. Cells were harvested by centrifugation at 4000 rpm at 4 C and resuspended in a buffer that consisted of 20 mMKH2PO4, 30 mM NaCl supplemented with protease inhibitors. Cells were lysed by six thirty-second sonication pulses in ice bath. Cell lysates were cleared by centrifugation at 11000 rpm for 1 hr at 4 C. Raw lysate was loaded at room temperature onto Hi-Trap Ni-affinity column and washed with 5 bed volumes of 20 mM imidazole, 20 mM KH2PO4, pH 7.4 on AkTA-FPLC at a flow rate of 0.5 mL/min. His-tagged TS was obtained by linear gradient elution (20 mM-500 mM imidazole) at a flow rate of 0.5 mL/min. TS fractions typically eluted at 200 mM imidazole. TS fractions were collected and re-concentrated using AMICON ultrafiltration system with MWCO 10000 Da filter to a concentration greater than 10 mg/mL. Resulting concentrate was loaded onto G75 Sepharose size-exclusion column preequilibrated with 20 mM KH2PO4, pH 7.4. TS protein was eluted at a flow rate of 0.1 mL/min and single fraction with estimated molecular weight over 60 kDa was collected. Eluant was re-concentrated using Amicon system (30000 Da MWCO) and presence of active human TS was confirmed by SDS-PAGE and in vitro enzymatic assays. Recombinant human TS of over 95% purity and high enzymatic activity was used for all in vitro kinetics experiments. FIG. 3 shows a protein gel of pure recombinant TS after column purification.

Example 3: In Vitro Enzymatic Assays of Inhibitor Activity

Effects of top-scoring compounds on TS activity in vitro were measured using a previously described spectrophotometric assay with minor modifications [32]. Specifically, assay mix consisted of 50 mM TES, 25 mM $MgCl_2$, 6.5 mM HCOH, 1.0 mM EDTA, 75 mM BME, 150 µM THF and 450 µM dUMP. Full-length human recombinant TS with N-terminal His-tag was purified in our laboratory and combined with 10 µM candidate compounds in 96-well plates at room temperature (25° C.). Effects of the compounds on kinetic parameters were measured at 37° C. under saturating substrate conditions by monitoring change in absorbance at 340 nm at 15 second intervals for 15 minutes. The enzyme concentration (0.5-1.0 ug/mL) was used throughout all kinetics experiments.

Example 4: Cell Culture and Cell Viability Assays of Inhibitor Activity 27 top scoring compounds that were identified by in silico screening were tested in human cancer cell lines. Cancer cell lines used for inhibitor testing were maintained under 70% confluency in appropriate cell culture medium (typically DMEM, supplemented with 10% FBS, and 1% pen-strep). Small molecule compounds were obtained from NCI DTP, resuspended in DMSO to generate 50 mM stocks and stored in the dark. In all experiments, fresh compound preparations were used whenever possible and no more than 2 freeze-thaw cycles were allowed for all drug tested. Cells were seeded in 96-well plates in quadruplicates (4 wells/condition) at 4000 cells/well. Compound solutions were freshly prepared in the appropriate cell culture medium and were added the following morning to the cells. After 72-hour incubation with the compound, cell proliferation was measured by MTS assays (Promega) and compared to that of the untreated cells or control drug, such as 5-FU or pemetrexed. Dose-response parameters were determined by plotting percent cell proliferation after treatment from at least eight different compound concentrations and by using non-linear regression fit (4-parameter dose-response) in Sigmaplot. All results shown are representative of at least 3 independent experiments.

Example 5: Maximum Tolerated Doses for New Ts Inhibitors

To establish the maximum tolerated dose (MTD), both immunodeficient SCID and immunocompetent FVB.129 mice were i.p. injected daily with compounds S and methylated derivative of compound S at 12.5, 50, and 100 MKG (mg/kg) (Table 4 and 5). The SCID immunodeficient mice were i.p. injected daily for 3 weeks and kept under observation for one additional week. Animals' weights were measured daily and the data are presented as the percentage of weight change from day 1 of treatment to day 28 at the termination of the experiment (Table 4). The MTD for SCID mice for both compounds was 50 MKG. The FVB.129 immunocompetent mice were i.p. injected daily for 2 weeks and kept under observation for one additional week. Animals' weights were measured daily and the data are presented as the percentage of weight change from day 1 of treatment to day 21 at the termination of the experiment (Table 5). The FVB.129 mice appeared healthy when treated up to 100 MKG with methylated derivative of compound S, while animals treated with compound S died at 50 MKG at day 6 after treatment. Thus, we have identified a derivative of compounds S that is less toxic to immunocompetent FVB.129 mice.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

[1] P. V. Danenberg, Thymidylate synthetase—a target enzyme in cancer chemotherapy, Biochimica et biophysica acta, 473 (1977) 73-92.

[2] S. Ramaswamy, P. Tamayo, R. Rifkin, S. Mukherjee, C. H. Yeang, M. Angelo, C. Ladd, M. Reich, E. Latulippe, J. P. Mesirov, T. Poggio, W. Gerald, M. Loda, E. S. Lander, T. R. Golub, Multiclass cancer diagnosis using tumor gene expression signatures, Proceedings of the National Academy of Sciences of the United States of America, 98 (2001) 15149-15154.

[3] J. M. Grunda, L. B. Nabors, C. A. Palmer, D. C. Chhieng, A. Steg, T. Mikkelsen, R. B. Diasio, K. Zhang, D. Allison, W. E. Grizzle, W. Wang, G. Y. Gillespie, M. R. Johnson, Increased expression of thymidylate synthetase (TS), ubiquitin specific protease 10 (USP10) and survivin is associated with poor survival in glioblastoma multiforme (GBM), J Neurooncol, 80 (2006) 261-274.

[4] M. Aarhus, O. Bruland, G. Bredholt, H. Lybaek, E. S. Husebye, B. K. Krossnes, C. Vedeler, K. Wester, M. Lund-Johansen, P. M. Knappskog, Microarray analysis reveals down-regulation of the tumour suppressor gene WWOX and up-regulation of the oncogene TYMS in intracranial sporadic meningiomas, J Neurooncol, (2008).

[5] P. Ceppi, M. Volante, S. Saviozzi, I. Rapa, S. Novello, A. Cambieri, M. Lo Iacono, S. Cappia, M. Papotti, G. V. Scagliotti, Squamous cell carcinoma of the lung compared with other histotypes shows higher messenger RNA and protein levels for thymidylate synthase, Cancer, 107 (2006) 1589-1596.

[6] P. Ceppi, M. Volante, A. Ferrero, L. Righi, I. Rapa, R. Rosas, A. Berruti, L. Dogliotti, G. V. Scagliotti, M. Papotti, Thymidylate synthase expression in gastroenteropancreatic and pulmonary neuroendocrine tumors, Clin Cancer Res, 14 (2008) 1059-1064.

[7] C. F. Skibola, M. S. Forrest, F. Coppede, L. Agana, A. Hubbard, M. T. Smith, P. M. Bracci, E. A. Holly, Polymorphisms and haplotypes in folate-metabolizing genes and risk of non-Hodgkin lymphoma, Blood, 104 (2004) 2155-2162.

[8] L. Rahman, D. Voeller, M. Rahman, S. Lipkowitz, C. Allegra, J. C. Barrett, F. J. Kaye, M. Zajac-Kaye, Thymidylate synthase as an oncogene: a novel role for an essential DNA synthesis enzyme, Cancer cell, 5 (2004) 341-351.

[9] D. Voeller, L. Rahman, M. Zajac-Kaye, Elevated levels of thymidylate synthase linked to neoplastic transformation of mammalian cells, Cell Cycle, 3 (2004) 1005-1007.

[10] D. Edler, M. Hallstrom, P. G. Johnston, I. Magnusson, P. Ragnhammar, H. Blomgren, Thymidylate synthase expression: an independent prognostic factor for local recurrence, distant metastasis, disease-free and overall survival in rectal cancer, Clinical cancer research: an official journal of the American Association for Cancer Research, 6 (2000) 1378-1384.

[11] D. B. Longley, D. P. Harkin, P. G. Johnston, 5-fluorouracil: mechanisms of action and clinical strategies, Nat Rev Cancer, 3 (2003) 330-338.

[12] M. Spielmann, M. Martin, M. Namer, A. duBois, C. Unger, D. J. Dodwell, Activity of pemetrexed (ALIMTA, multitargeted antifolate, LY231514) in metastatic breast cancer patients previously treated with an anthracycline and a taxane: an interim analysis, Clinical breast cancer, 2 (2001) 47-51.

[13] R. Labianca, L. Milesi, S. Mosconi, M. A. Pessi, G. D. Beretta, A. Quadri, The role of adjuvant chemotherapy in colon cancer, Surgical oncology, 16 Suppl 1 (2007) S93-96.

[14] C. X. Ma, P. Steen, K. M. Rowland, R. D. Niedringhaus, T. R. Fitch, J. W. Kugler, D. W. Hillman, E. A. Perez, J. N. Ingle, A. A. Adjei, A phase II trial of a combination of pemetrexed and gemcitabine in patients with metastatic breast cancer: an NCCTG study, Annals of oncology: official journal of the European Society for Medical Oncology/ESMO, 17 (2006) 226-231.

[15] M. Medinger, S. Steinbild, K. Mross, [Adjuvant and palliative anticancer treatment of colon carcinoma in 2004], Praxis, 93 (2004) 1633-1644.

[16] E. Galvani, G. J. Peters, E. Giovannetti, Thymidylate synthase inhibitors for non-small cell lung cancer, Expert Opin Investig Drugs, 20 (2011) 1343-1356.

[17] F. Barlesi, R. Gervais, H. Lena, J. Hureaux, H. Berard, D. Paillotin, S. Bota, I. Monnet, A. Chajara, G. Robinet, Pemetrexed and cisplatin as first-line chemotherapy for advanced non-small-cell lung cancer (NSCLC) with asymptomatic inoperable brain metastases: a multicenter phase II trial (GFPC 07-01), Annals of oncology: official journal of the European Society for Medical Oncology/ESMO, 22 (2011) 2466-2470.

[18] S. Copur, K. Aiba, J. C. Drake, C. J. Allegra, E. Chu, Thymidylate synthase gene amplification in human colon cancer cell lines resistant to 5-fluorouracil, Biochemical pharmacology, 49 (1995) 1419-1426.

[19] J. Sigmond, H. H. Backus, D. Wouters, O. H. Temmink, G. Jansen, G. J. Peters, Induction of resistance to the multitargeted antifolate Pemetrexed (ALIMTA) in WiDr human colon cancer cells is associated with thymidylate synthase overexpression, Biochemical pharmacology, 66 (2003) 431-438.

[20] E. Chu, J. C. Drake, D. M. Koeller, S. Zinn, C. A. Jamis-Dow, G. C. Yeh, C. J. Allegra, Induction of thymidylate synthase associated with multidrug resistance in human breast and colon cancer cell lines, Molecular pharmacology, 39 (1991) 136-143.

[21] B. Van Triest, H. M. Pinedo, G. Giaccone, G. J. Peters, Downstream molecular determinants of response to 5-fluorouracil and antifolate thymidylate synthase inhibitors, Annals of oncology: official journal of the European Society for Medical Oncology/ESMO, 11 (2000) 385-391.

[22] C. W. Carreras, D. V. Santi, The catalytic mechanism and structure of thymidylate synthase, Annu Rev Biochem, 64 (1995) 721-762.

[23] J. Phan, S. Koli, W. Minor, R. B. Dunlap, S. H. Berger, L. Lebioda, Human thymidylate synthase is in the closed conformation when complexed with dUMP and raltitrexed, an antifolate drug, Biochemistry, 40 (2001) 1897-1902.

[24] J. J. Irwin, T. Sterling, M. M. Mysinger, E. S. Bolstad, R. G. Coleman, ZINC: A Free Tool to Discover Chemistry for Biology, J Chem Inf Model, (2012).

[25] C. A. Lipinski, Drug-like properties and the causes of poor solubility and poor permeability, Journal of pharmacological and toxicological methods, 44 (2000) 235-249.

[26] A. J. Wahba, M. Friedkin, The enzymatic synthesis of thymidylate. I. Early steps in the purification of thymidylate synthetase of *Escherichia coli*, The Journal of biological chemistry, 237 (1962) 3794-3801.

[27] G.-E. N. Sittampalam G S, Arkin M Assay Guidance Manual, in: G. S. Sittampalam, N. Gal-Edd, M. Arkin, D. Auld, C. Austin, B. Bejcek, M. Glicksman, J. Inglese, V. Lemmon, Z. Li, J. McGee, O. McManus, L. Minor, A. Napper, T. Riss, O. J. Trask, J. Weidner (Eds.) Assay Guidance Manual, Bethesda (Md.), 2004.

[28] G. Klebe, Virtual ligand screening: strategies, perspectives and limitations, Drug discovery today, 11 (2006) 580-594.

[29] S. Mukherjee, T. E. Balius, R. C. Rizzo, Docking validation resources: protein family and ligand flexibility experiments, J Chem Inf Model, 50 (2010) 1986-2000.

[30] S. R. Brozell, S. Mukherjee, T. E. Balius, D. R. Roe, D. A. Case, R. C. Rizzo, Evaluation of DOCK 6 as a pose generation and database enrichment tool, J Comput Aided Mol Des, 26 (2012) 749-773.

[31] D. Cardinale, G. Guaitoli, D. Tondi, R. Luciani, S. Henrich, O. M. Salo-Ahen, S. Ferrari, G. Marverti, D. Guerrieri, A. Ligabue, C. Frassineti, C. Pozzi, S. Mangani, D. Fessas, R. Guerrini, G. Ponterini, R. C. Wade, M. P. Costi, Protein-protein interface-binding peptides inhibit the cancer therapy target human thymidylate synthase, Proc Natl Acad Sci USA, 108 (2011) E542-549.

[32] A. J. Wahba, M. Friedkin, Direct spectrophotometric evidence for the oxidation of tetrahydrofolate during the enzymatic synthesis of thymidylate, The Journal of biological chemistry, 236 (1961) PC11-12.

We claim:

1. A method for treating cancer in a subject comprising administering an effective amount of a composition comprising one or more thymidylate synthase inhibitor, wherein said one or more thymidylate synthase inhibitor is a compound, selected from the group consisting of:

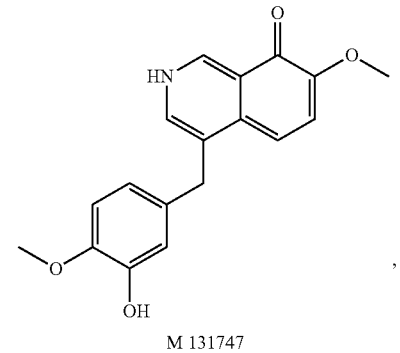

M 131747

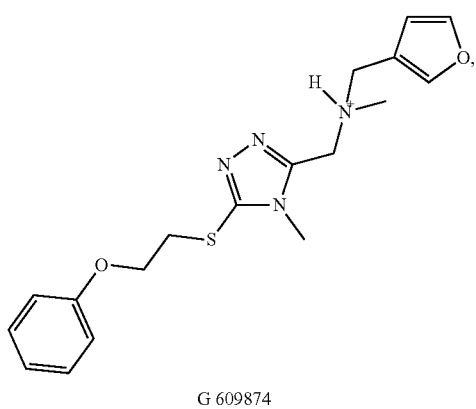

G 609874

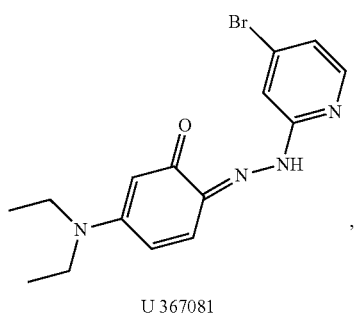 [SMILES: CCN(CC)C1=CC(=O)/C(=N/Nc2cc(Br)ccn2)C=C1]

U 367081 and salts thereof,
wherein the cancer is lung cancer, pancreatic cancer, cervical cancer, or hematopoietic cancer.

2. The method of claim 1, wherein the one or more thymidylate synthase inhibitor is selective for cancer cells.

3. The method of claim 1, wherein the one or more thymidylate synthase inhibitor is a compound selected from the group consisting of:

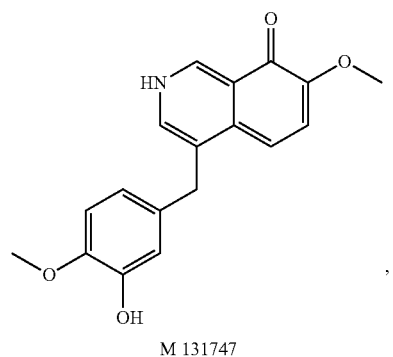

M 131747 and a salt thereof.

4. The method of claim 1, wherein the method further comprises administering radiation therapy and/or at least one additional anti-cancer agent.

5. The method of claim 4, wherein the anti-cancer agent is a chemotherapeutic agent selected from the group consisting of anthracyclines; platinum-based chemotherapy drugs; 5-fluorouracil (5-FU), cytarabine, floxuridine; biologic agents, kinase inhibitors; alkylating agents, and combinations thereof.

6. The method of claim 5, wherein the chemotherapeutic agent is:
   a) an anthracycline selected from the group consisting of doxorubicin, epirubicin, daunorubicin, aclarubicin, idarubicin, amrubicin, pirarubicin, valrubicin, zorubicin, carminomycin, and detorubicin;
   b) a platinum-based chemotherapy drug selected from the group consisting of carboplatin, cisplatin, nedaplatin, oxaliplatin, triplatin tetranitrate, and satraplatin;
   c) a compound selected from the group consisting of 5-fluorouracil (5-FU), cytarabine, and floxuridine;
   d) an alkylating agent selected from the group consisting of cyclophosphamide, chlorambucil, uramustine, ifosfamide, melphalan, bendamustine; nitrosourea compounds; busulfan; dacarbazine; procarbazine; altretamine; mitozolomide; and temozolomide;
   e) biologic agents selected from the group consisting of epotin, opreleukin, filgrastim, pegfilgrastim, rituximab, trastuzumab, and aldesleukin; or
   f) a tyrosine kinase inhibitor selected from the group consisting of sorafenib, sunitinib and imatinib.

7. The method of claim 1, wherein the hematopoietic cancer is acute lymphoblatic leukemia (ALL), acute myelogenous leukemia (AML), acute promyelocytic leukemia, chronic lymphocytic leukemia (CLL), chronic myelogenous leukemia (CML), acute monocytic leukemia (AMOL), hairy cell leukemia, large cell immunoblastic lymphoma, plasmacytoma, multiple myeloma, Hodgkin's lymphoma, or non-Hodgkin's lymphoma.

8. The method of claim 1, wherein the subject is human.

9. The method of claim 6, wherein the nitrosourea compounds are selected from the group consisting of the group consisting of carmustine, lomustine, semustine, and streptozotocin.

10. A method for treating cancer in a subject comprising administering an effective amount of a composition comprising one or more thymidylate synthase inhibitor, wherein said one or more thymidylate synthase inhibitor is a compound, selected from the group consisting of:

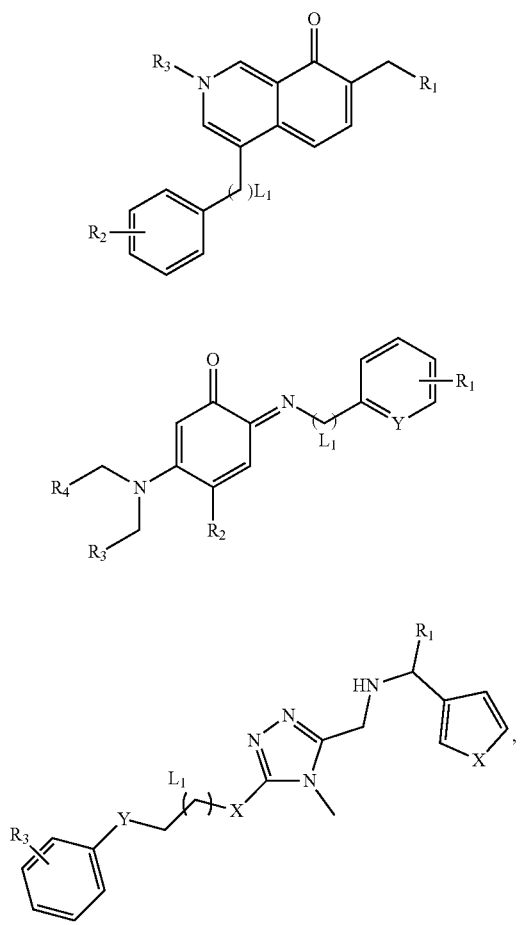

and salts thereof, wherein

R$_1$, R$_3$, R$_4$, and R$_5$ are independently, a hydrogen atom, methyl, C$_1$-C$_5$ branched or unbranched alkyl, amino, nitro, amidino, sulpho, sulphonamido, carboxy, cyano, phenyl, thienyl, pyrril, pyrazolyl, imidazolyl, isoxazyl, triazolyl, tetrazolyl, thiazolyl, oxazolyl, quinazolyl, pyridyl, pyrimidyl group, C$_1$-C$_5$ alkenyl, C$_1$-C$_5$ alkylamino, C$_2$-C$_{10}$ dialkylamino, hydroxy C$_1$-C$_5$ alkyl, carbonyl, C$_3$-C$_7$ cycloalkyl or trifluoromethyl group;

R$_2$ is a hydrogen atom, C$_1$-C$_5$ alkyl, hydroxy, amino, sulpho, sulphonamido, carboxy, or cyano group;

X is a carbon, nitrogen, oxygen or sulphur atom at the indicated position;

Y is a carbon, nitrogen or oxygen atom at the indicated position;

and

L$_1$ and L$_2$ are each independently C$_1$-C$_5$ alkylene, C$_2$-C$_5$ alkenylene, amidino, or ureido linker; and wherein the cancer is lung cancer, pancreatic cancer, cervical cancer, or hematopoietic cancer.

11. The method of claim 10, wherein the one or more thymidylate synthase inhibitor is a compound selected from the group consisting of:

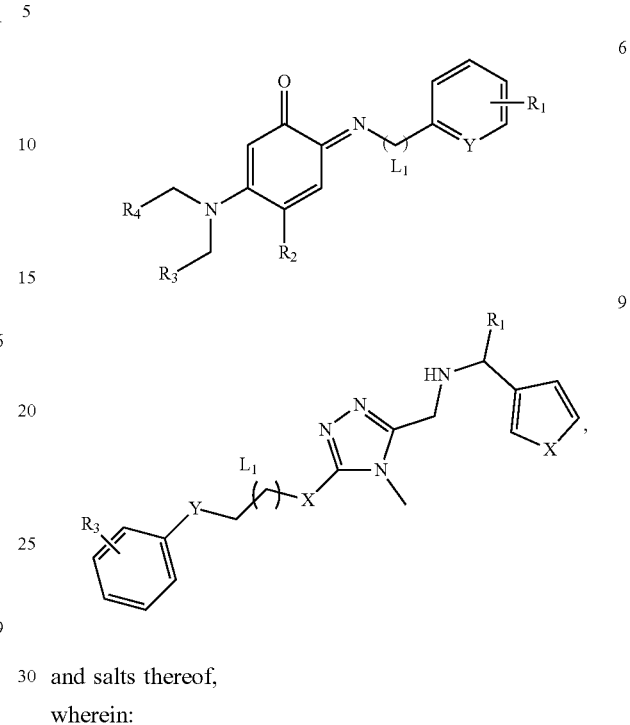

and salts thereof, wherein:

R$_1$, R$_3$, R$_4$, and R$_5$ are independently, a hydrogen atom, methyl, C$_1$-C$_5$ branched or unbranched alkyl, amino, nitro, amidino, sulpho, sulphonamido, carboxy, cyano, phenyl, thienyl, pyrril, pyrazolyl, imidazolyl, isoxazyl, triazolyl, tetrazolyl, thiazolyl, oxazolyl, quinazolyl, pyridyl, pyrimidyl group, C$_1$-C$_5$ alkenyl, C$_1$-C$_5$ alkylamino, C$_2$-C$_{10}$ dialkylamino, hydroxy C$_1$-C$_5$ alkyl, carbonyl, C$_3$-C$_7$ cycloalkyl or trifluoromethyl group;

R$_2$ is a hydrogen atom, C$_1$-C$_5$ alkyl, hydroxy, amino, sulpho, sulphonamido, carboxy, or cyano group;

X is a carbon, nitrogen, oxygen or sulphur atom at the indicated position;

Y is a carbon, nitrogen or oxygen atom at the indicated position; and

L$_1$ and L$_2$ are each independently C$_1$-C$_5$ alkylene, C$_2$-C$_5$ alkenylene, amidino, or ureido linker.

12. The method of claim 11, wherein the one or more thymidylate synthase inhibitor compounds is selected from the group consisting of:

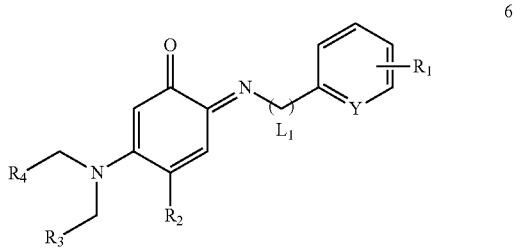

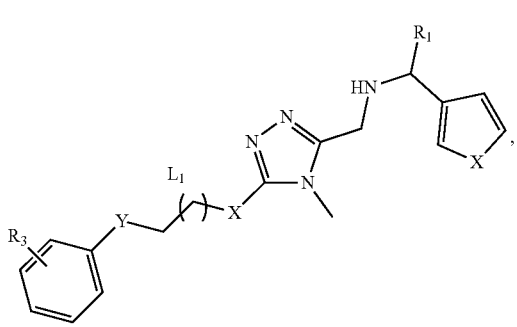

and salts thereof,
wherein:
- $R_1$, $R_3$, $R_4$, and $R_5$ are independently, a hydrogen atom, methyl, $C_1$-$C_5$ branched or unbranched alkyl, amino, nitro, amidino, sulpho, sulphonamido, carboxy, cyano, phenyl, thienyl, pyrril, pyrazolyl, imidazolyl, isoxazyl, triazolyl, tetrazolyl, thiazolyl, oxazolyl, quinazolyl, pyridyl, pyrimidyl group, $C_1$-$C_5$ alkenyl, $C_1$-$C_5$ alkylamino, $C_2$-$C_{10}$ dialkylamino, hydroxy $C_1$-$C_5$ alkyl, carbonyl, $C_3$-$C_7$ cycloalkyl or trifluoromethyl group;
- $R_2$ is a hydrogen atom, $C_1$-$C_5$ alkyl, hydroxy, amino, sulpho, sulphonamido, carboxy, or cyano group;
- X is a carbon, nitrogen, oxygen, or sulphur atom at the indicated position;
- Y is a carbon, nitrogen or oxygen atom at the indicated position; and
- $L_1$ and $L_2$ are each independently $C_1$-$C_5$ alkylene, $C_2$-$C_5$ alkenylene, amidino, or ureido linker.

13. The method of claim 1, wherein the cancer is a hematopoietic cancer.

14. The method of claim 1, wherein the cancer overexpresses thymidylate synthase.

15. The method of claim 1, wherein the cancer is refractory cancer or drug resistant cancer.

16. The method of claim 1, wherein the one or more thymidylate synthase inhibitor is a compound of the formula:

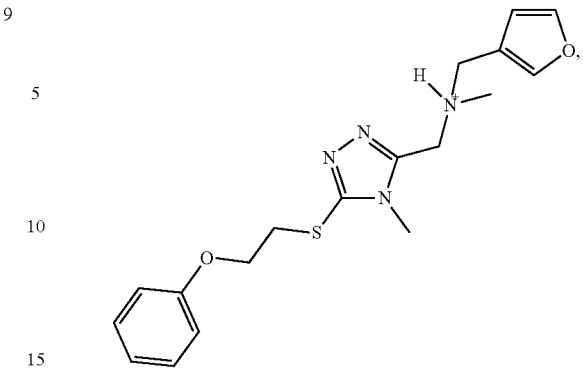

G 609874 and a salt thereof.

17. The method of claim 1, wherein the one or more thymidylate synthase inhibitor is a compound of the formula:

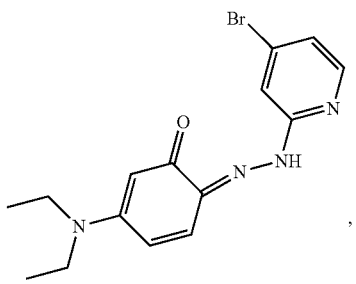

U 367081 and a salt thereof.

* * * * *

UNITED STATES PATENT AND TRADEMARK OFFICE
CERTIFICATE OF CORRECTION

PATENT NO. : 10,420,761 B2
APPLICATION NO. : 14/773906
DATED : September 24, 2019
INVENTOR(S) : Maria Zajac-Kaye et al.

Page 1 of 1

It is certified that error appears in the above-identified patent and that said Letters Patent is hereby corrected as shown below:

On the Title Page

Item (73), should read:
(73) Assignee:  University of Florida Research Foundation, Incorporated, Gainesville, FL (US)

In the Claims

In Claim 10, at Column 35, Lines 57-61, the text:
"X is a carbon, nitrogen, oxygen or sulphur atom at the indicated position; Y is a carbon, nitrogen or oxygen atom at the indicated position;"
Should be replaced with the text:
--X is a carbon, nitrogen, oxygen, or sulphur atom at the indicated position; Y is a carbon, nitrogen, or oxygen atom at the indicated position;--

In Claim 11, at Column 36, Lines 45-49, the text:
"X is a carbon, nitrogen, oxygen or sulphur atom at the indicated position; Y is a carbon, nitrogen or oxygen atom at the indicated position;"
Should be replaced with the text:
--X is a carbon, nitrogen, oxygen, or sulphur atom at the indicated position; Y is a carbon, nitrogen, or oxygen atom at the indicated position;--

Signed and Sealed this
Thirtieth Day of June, 2020

Andrei Iancu
*Director of the United States Patent and Trademark Office*